United States Patent
Hyde et al.

(10) Patent No.: US 7,897,399 B2
(45) Date of Patent: *Mar. 1, 2011

(54) NITRIC OXIDE SENSORS AND SYSTEMS

(75) Inventors: Roderick A. Hyde, Redmond, WA (US);
Muriel Y. Ishikawa, Livermore, CA (US); Leif T. Stordal, Issaquah, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/005,132

(22) Filed: Dec. 21, 2007

(65) Prior Publication Data

US 2009/0112485 A1  Apr. 30, 2009

Related U.S. Application Data

(63) Continuation-in-part of application No. 11/981,743, filed on Oct. 30, 2007.

(51) Int. Cl.
*B01J 19/00* (2006.01)
(52) U.S. Cl. ........... 436/55; 435/286.1; 702/24; 602/1; 602/41; 600/40; 600/377; 604/23; 604/500; 607/88; 422/98; 422/186
(58) Field of Classification Search .......... 422/98, 422/186; 702/24; 604/23, 500; 600/40, 600/377; 602/1, 41; 607/88; 435/286.1; 436/55

See application file for complete search history.

(56) References Cited

U.S. PATENT DOCUMENTS

| | | | |
|---|---|---|---|
| 4,162,536 A | 7/1979 | Morley | |
| 4,210,697 A | 7/1980 | Adiletta | |
| 4,248,214 A | 2/1981 | Hannah et al. | |
| 4,919,149 A | 4/1990 | Stang | |
| 5,109,871 A | 5/1992 | Thornton | |
| 5,351,698 A | 10/1994 | Wheeler et al. | |
| 5,366,997 A | 11/1994 | Keefer et al. | |
| 5,374,710 A | 12/1994 | Tsien et al. | |
| 5,405,919 A | 4/1995 | Keefer et al. | |
| 5,530,263 A | 6/1996 | DiVincenzo | |
| 5,571,152 A | 11/1996 | Chen et al. | |
| 5,580,433 A | 12/1996 | Baker et al. | |
| 5,665,077 A | 9/1997 | Rosen et al. | |
| 5,676,963 A | 10/1997 | Keefer et al. | |
| 5,683,668 A | 11/1997 | Hrabie et al. | |
| 5,690,777 A | 11/1997 | Kuethe et al. | |

(Continued)

FOREIGN PATENT DOCUMENTS

DE  20115123 U1  6/2001

(Continued)

OTHER PUBLICATIONS

U.S. Appl. No. 12/008,708, Hyde et al.

(Continued)

*Primary Examiner* — Jill Warden
*Assistant Examiner* — Shogo Sasaki

(57) ABSTRACT

The present disclosure relates to nitric oxide sensors and systems. In some embodiments one or more devices are provided that include one or more nitric oxide sensors; one or more transmitters; and one or more controllers configured to transmit using the one or more transmitters one or more signals that are associated with controlling one or more nitric oxide generators.

42 Claims, 10 Drawing Sheets

U.S. PATENT DOCUMENTS

| | | |
|---|---|---|
| 5,736,152 A | 4/1998 | Dunn |
| 5,765,558 A | 6/1998 | Psaros et al. |
| 5,814,666 A | 9/1998 | Green et al. |
| 5,858,799 A | 1/1999 | Yee et al. |
| 5,900,433 A | 5/1999 | Igo et al. |
| 5,910,316 A | 6/1999 | Keefer et al. |
| 5,943,160 A | 8/1999 | Downing |
| 5,956,172 A | 9/1999 | Downing |
| 5,980,705 A | 11/1999 | Allen et al. |
| 5,994,444 A | 11/1999 | Trescony et al. |
| 6,000,398 A | 12/1999 | Alla et al. |
| 6,037,346 A | 3/2000 | Doherty, Jr. et al. |
| 6,080,110 A | 6/2000 | Thorgersen |
| 6,100,096 A | 8/2000 | Bollinger et al. |
| 6,103,765 A | 8/2000 | Neal |
| 6,127,363 A | 10/2000 | Doherty, Jr. et al. |
| 6,143,314 A | 11/2000 | Chandrashekar et al. |
| 6,149,606 A | 11/2000 | Alving et al. |
| 6,156,753 A | 12/2000 | Doherty, Jr. et al. |
| 6,182,661 B1 | 2/2001 | Solanki et al. |
| 6,190,704 B1 | 2/2001 | Murrell |
| 6,223,747 B1 | 5/2001 | Rudge et al. |
| 6,280,604 B1 | 8/2001 | Allen et al. |
| 6,287,601 B1 | 9/2001 | Russell |
| 6,306,609 B1 | 10/2001 | Lai |
| 6,308,708 B2 | 10/2001 | Strauss et al. |
| 6,321,751 B1 | 11/2001 | Strauss et al. |
| 6,327,074 B1 | 12/2001 | Bass et al. |
| 6,341,607 B1 | 1/2002 | Couvreur |
| 6,369,071 B1 | 4/2002 | Haj-Yehia |
| 6,432,077 B1 | 8/2002 | Stenzler |
| 6,436,470 B1 | 8/2002 | Iacocca et al. |
| 6,440,498 B2 | 8/2002 | Schaller |
| 6,451,337 B1 | 9/2002 | Smith et al. |
| 6,469,051 B2 | 10/2002 | Nagano et al. |
| 6,559,184 B2 | 5/2003 | Neal |
| 6,621,687 B2 | 9/2003 | Lewis, Jr. et al. |
| 6,635,273 B1 | 10/2003 | Loscalzo et al. |
| 6,635,415 B1 * | 10/2003 | Bollinger et al. ............... 435/4 |
| 6,636,652 B1 | 10/2003 | Kopelman et al. |
| 6,639,007 B2 | 10/2003 | Plamthottam |
| 6,651,667 B2 | 11/2003 | Osterberg |
| 6,673,338 B1 | 1/2004 | Arnold et al. |
| 6,673,871 B2 | 1/2004 | Warneke et al. |
| 6,696,072 B1 | 2/2004 | Podolski |
| 6,706,274 B2 | 3/2004 | Herrmann et al. |
| 6,743,249 B1 | 6/2004 | Alden |
| 6,747,062 B2 | 6/2004 | Murrell |
| 6,773,714 B2 | 8/2004 | Dunn et al. |
| 6,812,500 B2 | 11/2004 | Reeh et al. |
| 6,818,356 B1 | 11/2004 | Bates |
| 6,841,166 B1 | 1/2005 | Zhang et al. |
| 6,900,891 B2 | 5/2005 | Kopelman et al. |
| 6,943,166 B1 | 9/2005 | Pullman et al. |
| 6,983,751 B2 | 1/2006 | Osterberg |
| 6,994,934 B2 | 2/2006 | Stanish et al. |
| 7,052,711 B2 | 5/2006 | West et al. |
| 7,088,040 B1 | 8/2006 | Ducharme et al. |
| 7,105,502 B2 | 9/2006 | Arnold et al. |
| 7,105,607 B2 | 9/2006 | Chen |
| 7,122,046 B2 | 10/2006 | Augustine et al. |
| 7,122,529 B2 | 10/2006 | Ruane et al. |
| 7,144,655 B2 | 12/2006 | Jenson et al. |
| 7,181,174 B2 | 2/2007 | Fitzgibbon et al. |
| 7,181,261 B2 | 2/2007 | Silver et al. |
| 7,183,001 B1 | 2/2007 | Ederle et al. |
| 7,189,471 B2 | 3/2007 | Jankowksi et al. |
| 7,194,801 B2 | 3/2007 | Jenson et al. |
| 7,206,605 B2 | 4/2007 | Hattori |
| 7,210,817 B2 | 5/2007 | Lee et al. |
| 7,215,687 B2 | 5/2007 | Kawai et al. |
| 7,215,887 B2 | 5/2007 | Ternullo et al. |
| 7,217,882 B2 | 5/2007 | Walukiewicz et al. |
| 7,218,900 B2 | 5/2007 | Suzuki |
| 7,220,258 B2 | 5/2007 | Myhr |
| 7,227,956 B1 | 6/2007 | Onishi |
| 7,235,189 B2 | 6/2007 | Höhn et al. |
| 7,235,361 B2 | 6/2007 | Bawendi et al. |
| 7,235,505 B2 | 6/2007 | Gromelski et al. |
| 7,236,595 B1 | 6/2007 | Bean et al. |
| 7,238,628 B2 | 7/2007 | Demaray et al. |
| 7,245,894 B2 | 7/2007 | Sekiguchi et al. |
| RE39,785 E | 8/2007 | Fuse |
| 7,253,953 B2 | 8/2007 | Browning |
| 7,254,160 B2 | 8/2007 | Kawamoto et al. |
| 7,256,923 B2 | 8/2007 | Liu et al. |
| 7,257,327 B2 | 8/2007 | Small |
| 7,260,155 B2 | 8/2007 | Stonick et al. |
| 7,260,402 B1 | 8/2007 | Ahmed |
| 7,260,764 B2 | 8/2007 | Chen |
| 7,260,768 B1 | 8/2007 | Matsumoto et al. |
| 7,261,693 B2 | 8/2007 | Wilcox et al. |
| 7,264,602 B1 | 9/2007 | Longsworth |
| 7,273,567 B1 | 9/2007 | Wellinghoff et al. |
| 7,280,811 B2 | 10/2007 | Sugiyama et al. |
| 7,283,710 B2 | 10/2007 | Sano et al. |
| 7,294,678 B2 | 11/2007 | McGlothlin et al. |
| 7,294,779 B2 | 11/2007 | Watabe et al. |
| 7,295,737 B2 | 11/2007 | Moorjani et al. |
| 7,295,741 B2 | 11/2007 | Sako et al. |
| 7,298,605 B2 | 11/2007 | Itoh et al. |
| 7,298,977 B2 | 11/2007 | Ohsawa et al. |
| 7,301,751 B2 | 11/2007 | Lee et al. |
| 7,301,754 B1 | 11/2007 | Knowles |
| 7,303,333 B2 | 12/2007 | Yu |
| 2002/0022046 A1 | 2/2002 | Tedeschi et al. |
| 2002/0026937 A1 | 3/2002 | Mault |
| 2002/0055702 A1 | 5/2002 | Atala et al. |
| 2002/0068365 A1 | 6/2002 | Kuhrts |
| 2002/0138051 A1 | 9/2002 | Hole et al. |
| 2002/0165179 A1 | 11/2002 | Baker, Jr. |
| 2003/0009127 A1 * | 1/2003 | Trescony et al. ............... 604/23 |
| 2003/0039697 A1 | 2/2003 | Zhao et al. |
| 2003/0073133 A1 | 4/2003 | Leyland-Jones |
| 2003/0077243 A1 | 4/2003 | Fitzhugh et al. |
| 2003/0093143 A1 | 5/2003 | Zhao et al. |
| 2003/0165578 A1 | 9/2003 | Murrell |
| 2004/0009238 A1 | 1/2004 | Miller et al. |
| 2004/0013747 A1 | 1/2004 | Tucker et al. |
| 2004/0072360 A1 | 4/2004 | Naaman et al. |
| 2004/0081580 A1 | 4/2004 | Hole et al. |
| 2004/0193218 A1 | 9/2004 | Butler |
| 2004/0247640 A1 | 12/2004 | Zhao et al. |
| 2005/0079148 A1 | 4/2005 | Fitzhugh et al. |
| 2005/0136483 A1 | 6/2005 | Carlson |
| 2005/0181026 A1 | 8/2005 | Davis et al. |
| 2005/0220838 A1 | 10/2005 | Zhao et al. |
| 2005/0267090 A1 | 12/2005 | Mascharak |
| 2006/0074282 A1 | 4/2006 | Ward et al. |
| 2006/0134728 A1 | 6/2006 | MacDonald et al. |
| 2006/0206171 A1 | 9/2006 | Gertner et al. |
| 2006/0206173 A1 | 9/2006 | Gertner et al. |
| 2006/0275350 A1 | 12/2006 | Davis et al. |
| 2006/0280307 A1 | 12/2006 | Ikushima et al. |
| 2007/0065473 A1 | 3/2007 | Miller |
| 2007/0088316 A1 | 4/2007 | Stenzler et al. |
| 2007/0148117 A1 | 6/2007 | Davis et al. |
| 2007/0166357 A1 | 7/2007 | Shaffer et al. |
| 2007/0181444 A1 | 8/2007 | Bernstein et al. |
| 2007/0190122 A1 | 8/2007 | Davis et al. |
| 2007/0208395 A1 | 9/2007 | Leclerc et al. |
| 2007/0274874 A1 * | 11/2007 | Miller et al. ............... 422/164 |
| 2008/0069863 A1 | 3/2008 | Peters |
| 2008/0097282 A1 | 4/2008 | Hole et al. |
| 2008/0220048 A1 | 9/2008 | Chen et al. |
| 2008/0281383 A1 | 11/2008 | Butler |
| 2008/0286321 A1 | 11/2008 | Reneker et al. |
| 2008/0311163 A1 | 12/2008 | Peters |
| 2009/0081279 A1 | 3/2009 | Jezek et al. |
| 2009/0202617 A1 | 8/2009 | Ward et al. |
| 2009/0204057 A1 | 8/2009 | Woo et al. |
| 2009/0214624 A1 | 8/2009 | Smith et al. |
| 2010/0152683 A1 | 6/2010 | Lindgren et al. |
| 2010/0197802 A1 | 8/2010 | Jezek et al. |

FOREIGN PATENT DOCUMENTS

| | | |
|---|---|---|
| EP | 1 704 877 A1 | 9/2006 |
| WO | WO 92/09962 | 6/1992 |
| WO | WO 96/08966 A1 | 3/1996 |
| WO | WO 00/53193 | 9/2000 |
| WO | WO 01/10344 A1 | 2/2001 |
| WO | WO 02/17898 A2 | 3/2002 |
| WO | WO 02/057738 A2 | 7/2002 |
| WO | WO 03/086282 A2 | 10/2003 |
| WO | WO 2005/070008 A2 | 8/2005 |
| WO | WO 2005/112954 A1 | 12/2005 |
| WO | WO 2006/095193 A2 | 9/2006 |
| WO | WO 2006/100155 A1 | 9/2006 |
| WO | WO 2006/107122 A1 | 10/2006 |
| WO | WO 2006/108420 A1 | 10/2006 |
| WO | WO 2007/130702 A2 | 11/2007 |
| WO | WO 2008/046211 A1 | 4/2008 |
| WO | WO 2009/131931 A1 | 10/2009 |

OTHER PUBLICATIONS

U.S. Appl. No. 12/008,694, Hyde et al.
U.S. Appl. No. 12/006,090, Hyde et al.
U.S. Appl. No. 12/006,069, Hyde et al.
U.S. Appl. No. 12/006,049, Hyde et al.
Butler, P. et al.; "Cell Transplantation from Limb Allografts"; Plastic and Reconstructive Surgery; Bearing a date of Jul. 1998; pp. 161-168 (11 total pages); vol. 102, No. 1; American Society of Plastic Surgeons; located at: http://www.plasreconsurg.com; printed on Apr. 25, 2008.
Butler, A.R.; Nicholson, R.; *Life, Death and Nitric Oxide*; Bearing a date of Oct. 17, 2003; 1$^{st}$ edition; Royal Society of Chemistry; ISBN 978-0854046867.
U.S. Appl. No. 12/148,284, Hyde et al.
U.S. Appl. No. 12/148,283, Hyde et al.
De Lima, R.G. et al.; "Controlled Nitric Oxide Photo-Release From Nitro Ruthenium Complexes: The Vasodilator Response Produced by UV Light Irradiation"; Inorganica Chimica Acta; Bearing a date of 2005; pp. 2643-2650; vol. 358; Elsevier B.V.; located at: http://www.sciencedirect.com.
Frank, S. et al.; "Nitric Oxide Triggers Enhanced Induction of Vascular Endothelial Growth Factor Expression in Cultured Keratinocytes (HaCaT) and During Cutaneous Wound Repair"; The FASEB Journal; Bearing a date of 1999; pp. 2002-2014; vol. 13.
Ghaffari, A. et al.; "A Direct Nitric Oxide Gas Delivery System for Bacterial and Mammalian Cell Cultures"; Nitric Oxide; Bearing a date of 2005; pp. 129-140; vol. 12; Elsevier Inc.; located at: http://www.sciencedirect.com.
Ghaffari, A. et al.; "Efficacy of Gaseous Nitric Oxide in the Treatment of Skin and Soft Tissue Infections"; Wound Repair and Regeneration; Bearing a date of 2007; pp. 368-377; vol. 15; Wound Healing Society.
Ghaffari, A. et al.; "Potential Application of Gaseous Nitric Oxide as a Topical Antimicrobial Agent"; Nitric Oxide; Bearing a date of 2006; pp. 21-29; vol. 14; Elsevier Inc.; located at: http://www.sciencedirect.com.
Goldsmith, P.C. et al.; "Inhibitors of Nitric Oxide Synthase in Human Skin"; The Journal of Investigative Dermatology; Bearing a date of Jan. 1996; pp. 113-118; vol. 106, No. 1; The Society for Investigative Dermatology, Inc.
Govers, R.; Rabelink, T.J.; "Cellular Regulation of Endothelial Nitric Oxide Synthase"; Am. J. Physiol. Renal. Physiol.; Bearing a date of 2001; pp. F193-F206; vol. 280; The American Physiological Society; located at: http://www.ajprenal.org.
Guo, H.; "Two-and Three-Photon Upconversion of LaOBr:Er$^{3+}$"; Optical Materials; Bearing a date of 2007; pp. 1840-1843; vol. 29; Elsevier B.V.; located at: http://www.sciencedirect.com.
Hassett, D.J.; Imlay, J.A.; "Bactericidal Antibiotics and Oxidative Stress: A Radical Proposal"; ACS Chemical Biology; Bearing a date of 2007; pp. 708-710; vol. 2, No. 11; located at: http://www.acschemicalbiology.org.
Miller, C.C. et al.; "Treatment of Chronic Nonhealing Leg Ulceration with Gaseous Nitric Oxide: A Case Study"; Journal of Cutaneous Medicine and Surgery; Bearing a date of Aug. 2004; pp. 233-238; vol. 8, No. 4.

Pacher, P. et al.; "Nitric Oxide and Peroxynitrite in Health and Disease"; Physiol. Rev.; Bearing a date of Jan. 2007; pp. 315-424; vol. 87; The American Physiological Society; located at: http://www.prv.org.
Patel, D.N. et al.; "Spectroscopic and Two-Photon Upconversion Studies of Ho$^{3+}$—Doped Lu$_3$Al$_5$O$_{12}$"; Optical Materials; Bearing a date of Jul. 1998; pp. 225-234; vol. 10; Elsevier Science B.V.
Rapaport, A. et al.; "Review of the Properties of Up-Conversion Phosphors for New Emissive Displays"; Journal of Display Technology; Bearing a date of Mar. 2006; pp. 68-78; vol. 2, No. 1; IEEE.
Romero-Graillet, C. et al.; "Nitric Oxide Produced by Ultraviolet-Irradiated Keratinocytes Stimulates Melanogenesis"; J. Clin. Invest.; Bearing a date of Feb. 1997; pp. 635-642; vol. 99, No. 4; The American Society of Clinical Investigation, Inc.
Seabra, A.B. et al.; "S-Nitrosoglutathione Incorporated in Poly(Ethylene Glycol) Matrix: Potential Use for Topical Nitric Oxide Delivery"; Nitric Oxide; Bearing a date of 2004; pp. 263-272; vol. 11; Elsevier Inc.; located at: http://www.sciencedirect.com.
Shabani, M. et al.; "Enhancement of Wound Repair with a Topically Applied Nitric Oxide-Releasing Polymer"; Wound Repair and Regeneration; Bearing dates of Jul.-Sep. 1996; pp. 353-362; vol. 4, No. 3; The Wound Healing Society.
Sussman, C.; *Wound Care: A Collaborative Practice Manual*; Bearing a date of Jan. 2007; ISBN 0781774446.
Suzuki, H.; Hewitt, C.W.; "Cell Transplantation from Limb Allografts: Discussion"; Plastic and Reconstructive Surgery; Bearing a date of Jul. 1998; pp. 169-170 (2 total pages); vol. 102, No. 1; American Society of Plastic Surgeons; located at: http://www.plasreconsurg.com; printed on May 2, 2008.
Tamir, S.; Tannenbaum, S.R.; "The Role of Nitric Oxide (NO) in the Carcinogenic Process"; Biochimica et Biophysica Acta; Bearing a date of 1996; pp. F31-F36; vol. 1288; Elsevier Science B.V.
Tu, H. et al.; "A Novel Electrochemical Microsensor for Nitric Oxide Based on Electropolymerized Film of o-Aminobenzaldehyde-Ethylene-Diamine Nickel"; Electroanalysis; Bearing a date of 1999; pp. 70-74; vol. 11, No. 1; Wiley-VCH.
Van Faassen, E.; Vanin, A. (Eds); *Radicals for Life: The Various Forms Nitric Oxide*; Bearing a date of Mar. 2007; 442 pages; ISBN 978-0-444-52236-8; Elsevier.
Weller, R. et al.; "Antimicrobial Effect of Acidified Nitrite on Dermatophyte Fungi, *Candida* and Bacterial Skin Pathogens"; Journal of Applied Microbiology; Bearing a date of 2001; pp. 648-652; vol. 90; The Society for Applied Microbiology.
Weller, R. et al.; "Nitric Oxide Is Generated on the Skin Surface by Reduction of Sweat Nitrate"; The Journal of Investigative Dermatology; Bearing a date of Sep. 1996; pp. 327-331; vol. 107, No. 3; The Society of Investigative Dermatology, Inc.
Yamasaki, K. et al.; "Reversal of Impaired Wound Repair in iNOS-Deficient Mice by Topical Adenoviral-Mediated iNOS Gene Transfer"; J. Clin. Invest.; Bearing a date of Mar. 1998; pp. 967-971; vol. 101, No. 5; The American Society for Clinical Investigation, Inc.; located at: http://www.jci.org.
Zhelyaskov, V.R.; Godwin, D.W.; "Photolytic Generation of Nitric Oxide Through a Porous Glass Partitioning Membrane"; Nitric Oxide: Biology and Chemistry; Bearing a date of 1998; pp. 454-459; vol. 2, No. 6; Article No. NO980195; Academic Press.
"Nanotechnology—the new Viagra?"; Nanowerk News; bearing a date of Apr. 26, 2009; p. 1; located at http://www.nanowerk.com/news/newsid=10273.php.
Andrews, Karen L. et al.; "A Photosensitive Vascular Smooth Muscle Store of Nitric Oxide in Mouse Aorta: No Dependence on Expression of Endothelial Nitric Oxide Synthase"; British Journal of Pharmacology; 2003; pp. 932-940; vol. 138; Nature Publishing Group.
Bonaventura, Daniella et al., "A Macrocyclic Nitrosyl Ruthenium Complex is a NO Donor that Induces Rat Aorta Relaxation"; Nitric Oxide; Mar. 2004; pp. 83-91 (p. 1); vol. 10, Issue 2; located at : http://www.sciencedirect.com; printed on Oct. 26, 2007 (Abstract Only).
Burrell, María A. et al.; "Detection of Nitric Oxide Synthase (NOS) in Somatostatin-Producing Cells of Human and Murine Stomach and Pancreas"; The Journal of Histochemistry and Cytochemistry; 1996; pp. 339-346; vol. 44, No. 4; The Histochemical Society, Inc.

Chmura, Antonina et al.; "The Role of Photoinduced Electron Transfer Processes in Photodegradation of the [Fe$_4$($\mu_3$-S)$_3$(NO)$_7$]$^-$ Cluster"; Nitric Oxide; Dec. 2006; pp. 370-379 (p. 1); vol. 15, Issue 4; located at: http://www.sciencedirect.com; printed on Oct. 26, 2007 (Abstract Only).

Chen, X; Gillis, CN; "Methylene Blue Enhanced Photorelaxation in Aorta, Pulmonary Artery and Corpus Cavernosum"; Biochem. Biophys. Res. Commun.; Jan. 29, 1993; pp. 559-563 (pp. 1-2); vol. 190, No. 2; located at: http://www.pubmed.gov; printed on Oct. 26, 2007 (Abstract Only).

Dujić, Željko et al; "Aerobic Exercise Before Diving Reduces Venous Gas Bubble Formation in Humans"; J. Physiol.; 2004; pp. 637-642; vol. 555.3; The Physiological Society.

"Easy Life II"; Photon Technology International; pp. 1-3; located at: http://www.pti-nj.com/EasyLife/easylife.html; printed on Oct. 6, 2007.

Ferezin, Camila Z. et al; "The Complex Trans--[RuCl([15]aneN$_{4)NO}$]$^{2+}$Induces Rat Aorta Relaxation by Ultraviolet Light Irradiation"; Nitric Oxide; Nov. 2005; pp. 170-175 (p. 1); vol. 13, Issue 3; located at: http://www.sciencedirect.com; printed on Oct. 26, 2007 (Abstract Only).

Flitney, FW et al.; "Iron-Sulphur Cluster Nitrosyls, a Novel Class of Nitric Oxide Generator: Mechanism of Vasodilator Action on Rat Isolated Tail Artery"; Br. J. Pharmacol.; Nov. 1992; pp. 842-848 (pp. 1-2); vol. 107, No. 3; located at: http://www.pubmed.gov; printed on Oct. 26, 2007 (Abstract Only).

Flitney, Frederick Werner; Megson, Ian L.; "Nitric Oxide and the Mechanism of Rat Vascular Smooth Muscle Photorelaxation"; J. Physiol.; 2003; pp. 819-828; vol. 550.3; The Physiological Society.

Flitney, FW et al.; "Vasodilator Responses of Rat Isolated Tail Artery Enhanced by Oxygen-Dependent, Photochemical Release of Nitric Oxide from Iron-Sulphur-Nitrosyls"; Br. J. Pharmacol.; Apr. 1996; pp. 1549-1557 (pp. 1-2); vol. 117, No. 7; located at: http://www.pubmed.gov; printed on Oct. 26, 2007 (Abstract Only).

Fukuhara, Kiyoshi et al.; "Photochemical Generation of Nitric Oxide from 6-Nitrobenzo[α]pyrene"; J. Am. Chem. Soc., 2001; pp. 8662-8666 (p. 1); vol. 123, No. 36; located at: http://pubs.acs.org/cgi-bin/abstract.cgi/jacsat/2001/123/i36/abs/ja0109038.html; printed on Oct. 26, 2007 (Abstract Only).

Gaston, Benjamin; "Summary: Systemic Effects of Inhaled Nitric Oxide"; Proceedings of the American Thoracic Society; 2006; pp. 170-172; vol. 3.

Gau, Jen-Jr et al.; "A MEMS Based Amperometric Detector for *E. coli* Bacteria Using Self-Assembled Monolayers"; Biosensors & Bioelectronics; 2001; pp. 745-755; vol. 16; Elsevier Science B.V.

Graham-Rowe, Duncan; "Photonic Fabrics Take Shape"; Nature Photonics; Jan. 2007; pp. 6-7; vol. 1; Nature Publishing Group.

Hardwick, J.B.J. et al.; "A Novel Method for the Delivery of Nitric Oxide Therapy to the Skin of Human Subjects Using a Semi-Permeable Membrane"; Clinical Science; 2001; pp. 395-400; vol. 100; The Biochemical Society and the Medical Research Society.

Hattenbach, Lars-Olof et al.; "Detection of Inducible Nitric Oxide Synthase and Vascular Endothelial Growth Factor in Choroidal Neovascular Membranes"; Ophthalmologica; 2002; pp. 209-214; vol. 216; S. Karger AG, Basel.

Hou, Yongchun et al.; "Nanomolar Scale Nitric Oxide Generation from Self-Assembled Monolayer Modified Gold Electrodes"; Chem. Commun.; 2000; pp. 1831-1832; The Royal Society of Chemistry.

Hrabie, Joseph A.; Keefer, Larry K.; "Chemistry of the Nitric Oxide-Releasing Diazeniumdiolate ("Nitrosohydroxylamine") Functional Group and Its Oxygen-Substituted Derivatives"; Chem. Rev.; 2002; pp. 1135-1154; vol. 102; American Chemical Society.

Ikeda, Osamu et al.; "Nitric Oxide Detection with Glassy Carbon Electrodes Coated with Charge-Different Polymer Films"; Sensors; Apr. 26, 2005; pp. 161-170; vol. 5; ISSN 1424-8220; MDPI.

"InNo-T Nitric Oxide Measurement System"; Warner Instruments; Bearing dates of 1998-2007; pp. 1-2; located at: http://www.warneronline.com/product_info.cfm?ID=220; printed on Oct. 24, 2007.

Keefer, Larry K.; "Nitric Oxide-Releasing Compounds: From Basic Research to Promising Drugs"; Chemtech; Aug. 1998; pp. 30-35 (pp. 1-8); vol. 28, No. 8; located at: http://pubs.acs.org/hotartcl/chemtech/98/aug/nitric.html; printed on Oct. 2, 2007; The American Chemical Society.

Khan, MA et al.; "The Effect of Superoxide Dismutase on Nitric Oxide-Mediated and Electrical Field-Stimulated Diabetic Rabbit Cavernosal Smooth Muscle Relaxation"; BJU Int.; Jan. 2001; pp. 98-103 (p. 1); vol. 87, No. 1; located at: http://www.pubmed.gov; printed on Sep. 27, 2007 (Abstract Only).

Kim, SC et al.; "Effects of Ultraviolet Light on the Tension of Isolated Human Cavernosal Smooth Muscle from Non-Diabetic and Diabetic Impotent Men"; Urol. Res.; 1997; pp. 149-152 (p. 1); vol. 25, No. 2; located at: http://www.pubmed.gov; printed on Sep. 27, 2007 (Abstract Only).

Kim, JH et al; "Mechanism of UV Light-Induced Photorelaxation in Isolated Rat Aorta"; J. Vet. Sci.; Dec. 2000; pp. 81-86 (p. 1); vol. 1, No. 2; located at: http://www.pubmed.gov; printed on Oct. 26, 2007 (Abstract Only).

LI, Chang Ming et al.; "Electrochemical Detection of Nitric Oxide on a SWCNT/RTIL Composite Gel Microelectrode"; Electroanalysis; 2006; pp. 713-718; vol. 18, No. 7; WILEY-VCH Verlag GmbH & Co. KGaA, Weinheim.

"Light-Emitting Diode (LED)"; Fiber Optics; Bearing a date of 2005; pp. 1-10; located at: http://www.fiber-optics.info/articles/LEDs.htm; printed on Oct. 6, 2007.

Lin, Hong-Yu et al.; "Side-Polished Multimode Fiber Biosensor Based on Surface Plasmon Resonance with Halogen Light"; Applied Optics; Feb. 10, 2007; pp. 800-806; vol. 46, No. 5; Optical Society of America.

Matthews, EK et al.; "Photon Pharmacology of an Iron-Sulphur Cluster Nitrosyl Compound Acting on Smooth Muscle"; Br. J. Pharmacol.; Sep. 1994; pp. 87-94 (p. 1); vol. 113, No. 1; located at: http://www.pubmed.gov; printed on Oct. 26, 2007 (Abstract Only).

Mendioroz, A. et al.; "Infrared to Visible and Ultraviolet Upconversion Processes in Nd$^{3+}$-Doped Potassium Lead Chloride Crystal"; Optical Materials; Sep. 2004; pp. 351-357 (p. 1); vol. 26, Issue 4; located at: http://www.sciencedirect.com; printed on Oct. 29, 2007 (Abstract Only).

Nablo, Brian J. et al.; "Inhibition of Implant-Associated Infections Via Nitric Oxide Release"; Biomaterials; Dec. 2005; pp. 6984-6990 (p. 1); vol. 26, Issue 34; located at: http://www.sciencedirect.com; printed on Oct. 26, 2007 (Abstract Only).

"NO Electrodes"; WPI-Europe-Biosensing-NO Electrodes; Bearing a date of Nov. 29, 2007; pp. 1-5; World Precision Instruments; located at: http://www.wpi-europe.com/products/biosensing/noelectrodes.htm; printed on Nov. 29, 2007.

"OL 770-LED: High-Speed LED Measurement System"; Bearing a date of 2001; pp. 1-6; located at: http://www.optroniclabs.com; Optronic Laboratories, Inc.

"Particulate Effects on Immunologic Function"; OST 1997AR; Bearing a date of 1997; pp. 1-2; located at: http://www.fda.gov/cdrh/ost/rpt97/0ST1997AR9.HTML; printed on Oct. 16, 2007.

Peng, H. et al.; "Ultraviolet Light-Emitting Diodes Operating in the 340 nm Wavelength Range and Application to Time-Resolved Fluorescence Spectroscopy"; Applied Physics Letters; Aug. 23, 2004; pp. 1436-1438 (p. 1); vol. 85, Issue 8; located at: http://scitation.aip.org; printed on Oct. 26, 2007 (Abstract Only).

Pou, SJ et al.; "Biological Studies of a Nitroso Compound that Releases Nitric Oxide Upon Illumination"; Molecular Pharmacology; Oct. 1, 1994; pp. 709-715 (p. 1); vo. 46, Issue 4; located at: http://molpharm.aspetjournals.org/cgi/content/abstract/46/4/709; printed on Oct. 26, 2007 (Abstract Only).

"Probes for Nitric Oxide (NO) Research"; EMD-Calbiochem: Nitric Oxide Probes; Bearing a date of 2007; pp. 1-2; Calbiochem, Novabiochem, & Novagen; located at: http://www.emdbiosciences.com/html/cbc/nitric_oxide_probes.htm; printed on Nov. 29, 2007.

Rathel, Thomas R. et al.; "Application of 4,5-Diaminofluorescein to Reliably Measure Nitric Oxide Released from Endothelial Cells In Vitro"; Biological Procedures Online; Jun. 2, 2003; pp. 136-142; vol. 5, No. 1.

Rotta, J.C.G. et al.; "Nitric Oxide Release from the S-Nitrosothiol Zinc Phthalocyanine Complex by Flash Photolysis"; Brazilian Journal of Medical and Biological Research; 2003; pp. 587-594; vol. 36, No. 5; located at: http://www.scielo.br/pdf/bjmbr/v36n5/4604.pdf.

Seo, K.K. et al.; "Synergistic Effects of Sildenafil on Relaxation of Rabbit and Rat Cavernosal Smooth Muscles when Combined with Various Vasoactive Agents"; BJU International; 2001; pp. 596-601; vol. 88.

Singh, Ravinder JIT et al.; "Photosensitized Decomposition of S-Nitrosothiols and 2-Methyl-2-Nitrosopropane Possible Use for Site-Directed Nitric Oxide Production"; FEBS Letters; 1995; pp. 47-51; vol. 360; Federation of European Biochemical Societies.

Smith, DJ et al.; "Nitric Oxide-Releasing Polymers Containing the [N(O)NO]-Group"; J. Med. Chem.; Mar. 1, 1996; pp. 1148-1156 (p. 1); vol. 39, No. 5; located at: http://www.pubmed.gov; printed on Oct. 26, 2007 (Abstract Only).

Sonoki, T. et al.; "Detection of Inducible Nitric Oxide Synthase (iNOS) mRNA by RT-PCR in ATL Patients and HTLV-1 Infected Cell Lines: Clinical Features and Apoptosis by NOS Inhibitor"; Leukemia; 1999; pp. 713-718; vol. 13; Stockton Press.

Wadsworth, Roger et al.; "Physiologically Relevant Measurements of Nitric Oxide in Cardiovascular Research Using Electrochemical Microsensors"; Journal of Vascular Research; 2006; pp. 70-85; vol. 43; S. Karger AG, Basel.

Wang, Peng George et al.; "Nitric Oxide Donors: Chemical Activities and Biological Applications"; Chem. Rev.; 2002; pp. 1091-1134 (pp. 1-53); vol. 102, No. 4; American Chemical Society; located at: http://pubs.acs.org/cgi-bin/abstract.cgi/chreay/2002/102/i04/abs/cr0000401.html; printed on Oct. 26, 2007.

Wang, Tianlong et al.; "Inhaled Nitric Oxide in 2003: A Review of its Mechanisms of Action"; Canadian Journal of Anesthesia; 2003; pp. 839-846; vol. 50, No. 8.

Williamson, David; "Study: Nitric Oxide-Releasing Materials Might Reduce Medical Implant Infections"; UNC News Services; Sep. 7, 2001; pp. 1-2; No. 416; located at: http://www.unc.edu/news/archives/sep01/schoen090701.htm; printed on Oct. 4, 2007.

Xie, Rong-Jun; "Highly Efficient White-Light-Emitting Diodes Fabricated with Short-Wavelength Yellow Oxynitride Phosphors"; Applied Physics Letters; Mar. 6, 2006; pp. 101104.1-101104.3 (pp. 1-2); vol. 88; located at: http://scitation.aip.org/;printed on Oct. 26, 2007 (Abstract Only).

Liu et al.; "Novel Delivery System for the Bioregulatory Agent Nitric Oxide"; Chemistry of Materials; bearing a date of 2009; pp. 5032-5041; vol. 21, No. 21; © 2009 American Chemical Society.

"Nitric oxide-releasing wrap for donor organs and cloth for therapeutic socks"; e! Science News; bearing a date of Jan. 6, 2010; pp. 1-2; located at http://esciencenews.com/articles/2010/01/06/nitric.oxide.releasing.wrap.donor.organs.and.cloth.therapeutic.socks; printed on Jan. 19, 2010.

"A Method of Nitric Oxide Delivery for Healing and Organ Preservation"; University of Texas at Dallas; bearing a date of May 18, 2009; p. 1; located at http://utdallas.technologypublisher.com/TechnologyProject.aspx?id=2302.

"Nanotechnology bandage speeds up healing"; Nanowerk News; Source: Akron Beacon Journal (Paula Schleis); bearing a date of Dec. 15, 2006; pp. 1-2; printed on Jul.14, 2009; located at http://www.nanowerk.com/news/newsid=1156.php.

Birkeland et al.; "On The Oxidation of Atmospheric Nitrogen in Electric Arcs"; Nature; bearing a date of 1898; pp. 98-116; No. 1,506, vol. 58.

Levine et al.; "A New, Highly Efficient Red-Emitting Cathodoluminescent Phosphor ($YVO_4$:Eu) For Color Television"; Applied Physics Letters; bearing a date of Sep. 15, 1964; pp. 1-3; vol. 5, No. 6.

Mellor, J. W.; "Modern Inorganic Chemistry"; excerpt from Modern Inorganic Chemistry; bearing a date of 1912; pp. 1-19; Longmans, Greene, and Co.

"The Shadow Mask and Aperture Grill"; The PC Guide; bearing a date of Apr. 17, 2001; pp. 1-3; © Copyright 1997-2004 Charles M. Kozierok; printed Oct. 6, 2009; located at http://www.pcguide.com/ref/crt/crtMask-c.html.

* cited by examiner

NITRIC OXIDE SENSORS AND SYSTEMS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/981,743, entitled Methods and Systems for Use of Photolyzable Nitric Oxide Donors, naming Roderick A. Hyde as inventor, filed 30 Oct. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/998,864, entitled Systems and Devices that Utilize Photolyzable Nitric Oxide Donors, naming Roderick A. Hyde as inventor, filed 30 Nov. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,045, entitled Systems and Devices Related to Nitric Oxide Releasing Materials, naming Roderick A. Hyde, Muriel Y. Ishikawa and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,065, entitled Devices and Systems that Deliver Nitric Oxide, naming Roderick A. Hyde, Muriel Y. Ishikawa and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,132, entitled Nitric Oxide Sensors and Systems, naming Roderick A. Hyde, Muriel Y. Ishikawa and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,136, entitled Devices Configured to Facilitate Release of Nitric Oxide, naming Roderick A. Hyde, Muriel Y. Ishikawa and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,170, entitled Condoms Configured to Facilitate Release of Nitric Oxide, naming Roderick A. Hyde, Muriel Y. Ishikawa and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,090, entitled Sleeves Configured to Facilitate Release of Nitric Oxide, naming Roderick A. Hyde, Muriel Y. Ishikawa and Lowell L. Wood, Jr. as inventors, filed 28 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,069, entitled Nitric Oxide Permeable Housings, naming Roderick A. Hyde, Muriel Y. Ishikawa and Lowell L. Wood, Jr. as inventors, filed 28 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,049, entitled Substrates for Nitric Oxide Releasing Devices, naming Roderick A. Hyde, Muriel Y. Ishikawa and Lowell L. Wood, Jr. as inventors, filed 28 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/008,694, entitled Nitric Oxide Permeable Housings, naming Roderick A. Hyde, Muriel Y. Ishikawa and Lowell L. Wood, Jr. as inventors, filed 11 Jan. 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to nitric oxide sensors and systems.

SUMMARY

In some embodiments one or more devices are provided that include one or more nitric oxide sensors and one or more transmitters configured to transmit one or more signals that are associated with controlling one or more nitric oxide generators. In addition to the foregoing, other aspects are described in the claims, drawings, and text forming a part of the present disclosure.

In some embodiments one or more systems are provided that include circuitry for operating one or more nitric oxide sensors and circuitry for operating one or more transmitters configured to transmit one or more signals that are associated with controlling one or more nitric oxide generators. In addition to the foregoing, other aspects are described in the claims, drawings, and text forming a part of the present disclosure.

In some embodiments one or more systems are provided that include means for operating one or more nitric oxide sensors and means for operating one or more transmitters configured to transmit one or more signals that are associated with controlling one or more nitric oxide generators. In addition to the foregoing, other aspects are described in the claims, drawings, and text forming a part of the present disclosure.

In some embodiments one or more systems are provided that include a signal-bearing medium bearing one or more instructions for operating one or more nitric oxide sensors and one or more instructions for operating one or more transmitters configured to transmit one or more signals that are associated with controlling one or more nitric oxide generators. In addition to the foregoing, other aspects are described in the claims, drawings, and text forming a part of the present disclosure.

In some embodiments, means include but are not limited to circuitry and/or programming for effecting the herein referenced functional aspects; the circuitry and/or programming can be virtually any combination of hardware, software, and/or firmware configured to effect the herein referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

DETAILED DESCRIPTION

Figure 1:
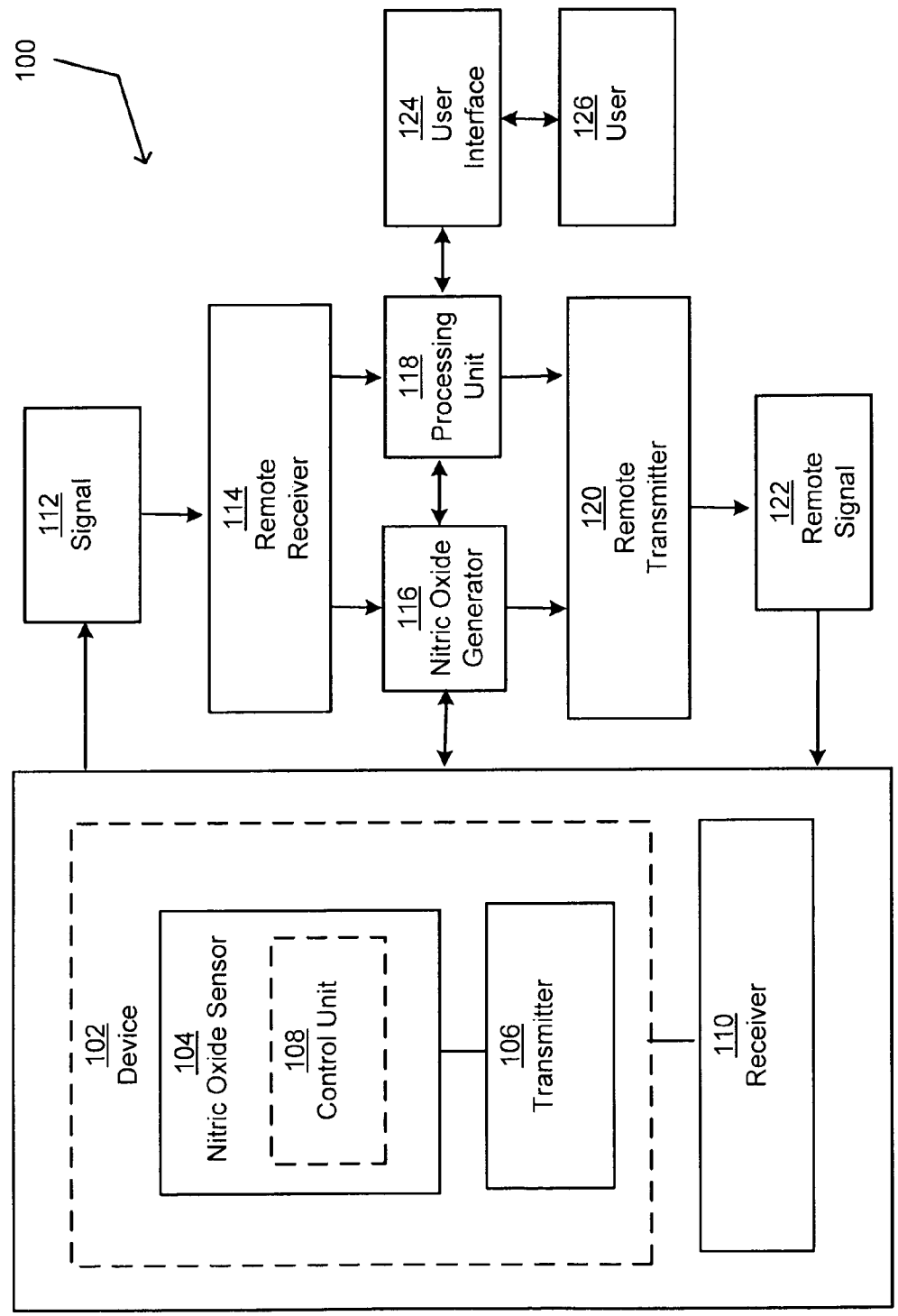
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates a system 100 in which embodiments may be implemented. System 100 may include one or more devices 102 that include one or more nitric oxide sensors 104 and one or more transmitters 106. In some embodiments, a device 102 may include one or more control units 108. In some embodiments, a device 102 may include one or more receivers 110. In some embodiments, device 102 may transmit one or more signals 112 that may be received by one or more remote receivers 114. In some embodiments, one or more signals 112 may include instructions for operating one or more nitric oxide generators 116. In some embodiments, one or more signals 112 may include one or more information packets. In some embodiments, system 100 may include one or more remote receivers 114 that are operably associated with one or more nitric oxide generators 116. In some embodiments, system 100 may include one or more remote receivers 114 that are operably associated with one or more processing units 118. In some embodiments, system 100 may include one or more processing units 118 that are operably associated with one or more user interfaces 124. In some embodiments, system 100 may include one or more user interfaces 124 that are operably associated with one or more nitric oxide generators 116. In some embodiments, system 100 may include one or more remote transmitters 120 that transmit one or more signals remote 122. In some embodiments, one or more remote signals 122 may include information related to the operation of one or more nitric oxide generators 116. In some embodiments, one or more remote signals 122 may include one or more information packets. In some embodiments, system 100 may include a device 102 that is configured to receive one or more remote signals 122 that are associated with one or more nitric oxide generators 116. In some embodiments, system 100 may include a device 102 that is configured to receive one or more remote signals 122 that are associated with one or more processing units 118. In some embodiments, system 100 may include a device 102 that is configured to receive one or more remote signals 122 that are associated with input of one or more users 126.

Device

Device 102 may be configured in numerous ways. In some embodiments, a device 102 may include one or more nitric oxide sensors 104 and one or more transmitters 106. In some embodiments, a device 102 may include one or more control units 108. In some embodiments, a device 102 may include one or more receivers 110. A device 102 may be operably associated with one or more nitric oxide generators 116. In some embodiments, a device 102 may receive one or more remote signals 122 that are transmitted by one or more remote transmitters 120 that are associated with one or more nitric oxide generators 116. In some embodiments, a device 102 may transmit one or more signals 112 with one or more transmitters 106. In some embodiments, one or more signals 112 may be received by one or more remote receivers 114. Accordingly, in some embodiments, one or more devices 102 may be in operable association with one or more nitric oxide generators 116. In some embodiments, one or more devices 102 and one or more nitric oxide generators 116 may operate in a coordinated fashion to generate nitric oxide in a controlled manner. For example, in some embodiments, one or more devices 102 and one or more nitric oxide generators 116 may operate in a coordinated manner to maintain the concentration of nitric oxide within a range of values within a space. In some embodiments, such a space may be an internal space associated with an individual. For example, in some embodiments, a device 102 may be configured to maintain nitric oxide at a concentration within penile tissue that is sufficient to sustain an erection. In some embodiments, such a space may be an external space associated with an individual. For example, in some embodiments, a device 102 may be associated with a bandage and/or patch that is configured to deliver nitric oxide to a skin surface that is beneath the bandage and/or patch when applied to an individual. Accordingly, in some embodiments, a device 102 and a nitric oxide generator 116 may operate to maintain an antibacterial concentration of nitric oxide within a space. In some embodiments, a device 102 may be configured for implantation into an individual. In some embodiments, a device 102 may be configured to detect nitric oxide within genital tissue of an individual. For example, in some embodiments, a device 102 may be configured to detect nitric oxide concentrations within genital tissue of a male individual. In some embodiments, a device 102 may be configured to detect nitric oxide in the vascular system of an individual. For example, in some embodiments, a device 102 may be configured to be implanted into venous tissue of an individual. In some embodiments, a device 102 may be configured to detect nitric oxide concentrations associated with an outside surface of an individual. In some embodiments, a device 102 may be configured to detect nitric oxide. In some embodiments, a device 102 may be configured to detect one or more nitric oxide synthases. In some embodiments, a device 102 may be configured to detect one or more nitric oxide donors. In some embodiments, a device 102 may be associated with one or more nitric oxide generators 116 through a hardwired connection. In some embodiments, a device 102 may be associated with one or more nitric oxide generators 116 through a wireless connection.

Nitric Oxide Sensor

Numerous types of nitric oxide sensors 104 may be used within system 100. In some embodiments, a device 102 may include one nitric oxide sensor 104. In some embodiments, a device 102 may include one or more nitric oxide sensors 104. In some embodiments, a nitric oxide sensor 104 may be configured for implantation into an individual (e.g., U.S. Pat. No. 7,181,261). For example, in some embodiments, one or more nitric oxide sensors 104 may be configured to be implanted into the genital region of an individual. Accordingly, in some embodiments, one or more nitric oxide sensors 104 may be used to determine the presence of nitric oxide in one or more tissues. In some embodiments, a nitric oxide sensor 104 may be configured for use on the outside surface of an individual. For example, in some embodiments, one or more nitric oxide sensors 104 may be configured to detect the concentration of nitric oxide on the surface of skin, a wound, a surface of a table, and the like. In some embodiments, one or more nitric oxide sensors 104 may be configured to be included within one or more housings. In some embodiments, one or more nitric oxide sensors 104 may be configured to be included within one or more nitric oxide permeable housings. In some embodiments, a nitric oxide sensor 104 may be configured to utilize fluorescence to detect nitric oxide. For example, in some embodiments, a nitric oxide sensor 104 may detect nitric oxide through use of one or more fluorescent probes, such as 4,5-diaminofluorescein diacetate (EMD Chemicals Inc., San Diego, Calif.). In some embodiments, a nitric oxide sensor 104 may detect nitric oxide through use of one or more electrodes. For example, in some embodiments, a nitric oxide sensor 104 may utilize an electrode that includes a single walled carbon nanotube and an ionic liquid to detect nitric oxide (e.g., Li et al., Electroanalysis, 18:713-718 (2006)). Numerous nitric oxide sensors 104 are commercially available and have been described (e.g., World Precision Instruments, Inc., Sarasota, Fla., USA; U.S. Pat. Nos. 6,100, 096; 6,280,604; 5,980,705). In some embodiments, a nitric oxide sensor 104 may include one or more transmitters 106. In some embodiments, a nitric oxide sensor 104 may include one or more receivers 110. In some embodiments, a nitric oxide sensor 104 may be configured to transmit one or more signals 112. In some embodiments, a nitric oxide sensor 104 may be configured to receive one or more remote signals 122.

In some embodiments, one or more nitric oxide sensors 104 may be configured to detect one or more nitric oxide synthases. In some embodiments, one or more nitric oxide sensors 104 may be configured to detect nitric oxide synthase activity. Nitric oxide synthase detection kits are commercially available (e.g., Cell Technology, Inc., Mountain View, Calif.). In some embodiments, one or more nitric oxide sensors 104 may be configured to detect nitric oxide synthase messenger ribonucleic acid (mRNA). Methods that may be used to detect such mRNA have been reported (e.g., Sonoki et al., Leukemia, 13:713-718 (1999)). In some embodiments, one or more nitric oxide sensors 104 may be configured to detect nitric oxide synthase through immunological methods. Methods that may be used to detect nitric oxide synthase been reported (e.g., Burrell et al., J. Histochem. Cytochem., 44:339-346 (1996) and Hattenbach et al., Ophthalmologica, 216:209-214 (2002)). In some embodiments, micro-electromechanical systems may be used to detect nitric oxide synthase. In some embodiments, antibodies and/or aptamers that bind to nitric oxide synthase may be used within one or more micro-electro-mechanical systems to detect nitric oxide synthase. Methods to construct micro-electro-mechanical detectors have been described (e.g., Gau et al., Biosensors 1070 & Bioelectronics, 16:745-755 (2001)). Accordingly, nitric oxide sensors 104 may be configured in numerous ways to detect one or more nitric oxide synthases.

In some embodiments, one or more nitric oxide sensors 104 may be configured to detect one or more nitric oxide donors. In some embodiments, one or more nitric oxide sensors 104 may include one or more surface plasmon resonance chemical electrodes that are configured to detect one or more nitric oxide donors. For example, in some embodiments, one or more nitric oxide sensors 104 may include one or more surface plasmon resonance chemical electrodes that include antibodies and/or aptamers that bind to one or more nitric oxide donors. Accordingly, such electrodes may be used to detect the one or more nitric oxide donors through use of surface plasmon resonance. Methods to construct surface plasmon resonance chemical electrodes are known and have been described (e.g., U.S. Pat. No. 5,858,799; Lin et al., Applied Optics, 46:800-806 (2007)). In some embodiments, antibodies and/or aptamers that bind to one or more nitric oxide donors may be used within one or more micro-electro-mechanical systems to detect one or more nitric oxide donors. Methods to construct micro-electro-mechanical detectors have been described (e.g., Gau et al., Biosensors & Bioelectronics, 16:745-755 (2001)).

Transmitter

The system 100 may include one or more transmitters 106. In some embodiments, system 100 ma include one or more remote transmitters 120. In some embodiments, a device 102 may include one or more transmitters 106 that transmit one or more signals 112 that are received by one or more nitric oxide generators 116. In some embodiments, system 100 may include one or more transmitters 106 that transmit one or more signals 112 that are associated with one or more nitric oxide generators 116. In some embodiments, one or more remote signals 122 that are associated with one or more nitric oxide generators 116 may be received by one or more devices 102. In some embodiments, the one or more remote signals 122 may be hardwired signals. In some embodiments, the one or more remote signals 122 may be wireless signals. In some embodiments, one or more transmitters 106 may be operably coupled to one or more nitric oxide sensors 104 through a hardwired connection. In some embodiments, one or more transmitters 106 may be operably coupled to one or more nitric oxide sensors 104 through a wireless connection. Numerous types of transmitters 106 and remote transmitters 120 may be used in association with system 100. Examples of such transmitters 106 and remote transmitters 120 include, but are not limited to, transmitters 106 and/or remote transmitters 120 that transmit one or more optical signals, radio signals, wireless signals, hardwired signals, infrared signals, ultrasonic signals, acoustic signals, and the like (e.g., U.S. Pat. Nos. RE39,785; 7,260,768; 7,260,764; 7,260,402; 7,257,327; 7,215,887; 7,218,900; herein incorporated by reference). In some embodiments, one or more transmitters 106 and/or remote transmitters 120 may transmit one or more signals 112 and/or remote signals 122 that are encrypted. Numerous types of transmitters are known and have been described (e.g., U.S. Pat. Nos. and Published U.S. Patent Application: 7,236,595; 7,260,155; 7,227,956; US2006/0280307; herein incorporated by reference).

Control Unit

System 100 may include one or more control units 108. In some embodiments, one or more control units 108 may be operably associated with one or more devices 102. In some embodiments, one or more control units 108 may be operably associated with one or more nitric oxide sensors 104. In some embodiments, one or more control units 108 may be operably associated with one or more receivers 110. In some embodiments, one or more control units 108 may be operably associated with one or more transmitters 106. In some embodiments, one or more control units 108 may be configured to control one or more operations of one or more devices 102. Examples of such operations include, but are not limited to, transmitting one or more signals 112, detecting nitric oxide, receiving one or more remote signals 122, and the like. In some embodiments, a control unit 108 may include memory. In some embodiments, a control unit 108 may include one or more programs that provide instructions for controlling one or more devices 102.

Receiver

System 100 may include one or more receivers 110. In some embodiments, system 100 may include one or more remote receivers 114. In some embodiments, one or more receivers 110 may be associated with one or more devices 102. In some embodiments, one or more remote receivers 114 may be associated with one or more nitric oxide generators 116. In some embodiments, one or more receivers 110 may be associated with one or more control units 108. Numerous types of receivers 110 and/or remote receivers 114 may be used in association with system 100. Examples of such receivers include, but are not limited to, receivers that receive one or more optical signals, radio signals, wireless signals, hardwired signals, infrared signals, ultrasonic signals, acoustic signals, and the like. Such receivers are known and have been described (e.g., U.S. Pat. Nos. RE39,785; 7,218,900; 7,254,160; 7,245,894; 7,206,605; herein incorporated by reference).

Signal

Numerous types of signals 112 and/or remote signals 122 may be used in association with system 100. Examples of such signals include, but are not limited to, optical signals, radio signals, wireless signals, hardwired signals, infrared signals, ultrasonic signals, and the like. In some embodiments, one or more signals 118 and/or remote signals 122 may not be encrypted. In some embodiments, one or more signals 112 and/or remote signals 122 may be encrypted. In some embodiments, one or more signals 112 and/or remote signals 122 may be sent through use of a secure mode of transmission. In some embodiments, one or more signals 112 and/or remote signals 122 may be coded for receipt by a specific individual. In some embodiments, such code may include anonymous code that is specific for an individual. Accordingly, information included within one or more signals 118 and/or remote signals 122 may be protected against being accessed by others who are not the intended recipient.

Processing Unit

System 100 may include one or more processing units 118. In some embodiments, a processing unit 118 may be configured to process information associated with one or more devices 102. In some embodiments, a processing unit 118 may be configured to process information associated with one or more nitric oxide generators 116. In some embodiments, a processing unit 118 may be configured to process information associated with one or more devices 102 and one or more nitric oxide generators 116. In some embodiments, a processing unit 118 may include one or more central processing units. In some embodiments, a processing unit 118 may include memory. In some embodiments, a processing unit 118 may include one or more programs. For example, in some embodiments, one or more programs may be configured to provide instructions associated with the operation of one or more devices 102. In some embodiments, one or more programs may be configured to provide instructions associated with the operation of one or more nitric oxide generators 116. In some embodiments, one or more programs may be configured to provide instructions associated with the operation of one or more nitric oxide generators 116 and one or more devices 102. Examples of instructions include, but are not limited to, instructions associated with one or more concentrations of nitric oxide to maintain within a space and/or tissue, instructions associated with one or more times when nitric oxide is to be generated, instructions associated with the duration of nitric oxide production, and the like. In some embodiments, a processing unit 118 may be operably associated with one or more user interfaces 124.

Nitric Oxide Generator

System 100 may include one or more nitric oxide generators 116. Numerous types of nitric oxide generators 116 may be used with system 100. In some embodiments, a nitric oxide generator 116 may produce nitric oxide in response to one or more signals 112. For example, in some embodiments, a nitric oxide generator 116 may include one or more light sources that are associated with one or more photolyzable nitric oxide donors such that illumination of the one or more light sources facilitates release of nitric oxide from the one or more photolyzable nitric oxide donors. In some embodiments, one or more nitric oxide generators 116 may include one or more nitric oxide donors that are activated chemically. Accordingly, in some embodiments, a nitric oxide generator 116 may be configured to mix two or more reactants to generate nitric oxide. In some embodiments, one or more nitric oxide generators 116 may include one or more nitric oxide donors that are coupled to a conductive substrate such that passage of electrical current through the conductive substrate will generate nitric oxide (e.g., Hou et al., Chem. Commun., 1831-1832 (2000)). Numerous methods that may be used to generate nitric oxide have been described (e.g., U.S. Pat. No. 5,814,666; U.S. Published Patent Application No.: 2007/0088316). In some embodiments, a nitric oxide generator 116 may be configured for implantation within an individual. In some embodiments, a nitric oxide generator 116 may be configured to administer nitric oxide to a surface of an individual. For example, in some embodiments, a nitric oxide generator 116 may be configured to apply nitric oxide to a skin surface of an individual.

User Interface/User

System 100 may include numerous types of user interfaces 124. For example, one or more users 126 (e.g., individuals) may interact through use of numerous user interfaces 124 that utilize hardwired methods, such as through use of an on/off switch, a push button, a keyboard, and the like. In some embodiments, the user interface 124 may utilize wireless methods, such as methods that utilize a transmitter and receiver, utilize the internet, and the like.

Figure 2:
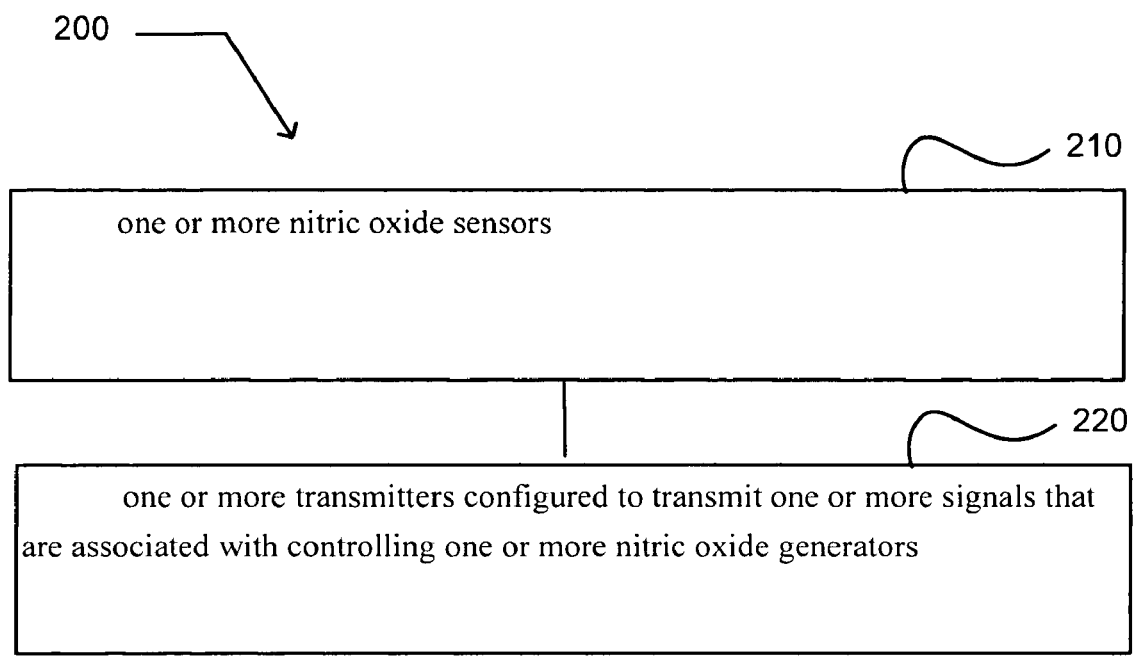
FIG. 2 illustrates embodiment 200 of device 102 within system 100.

FIG. 2 illustrates embodiment 200 of device 102 within system 100. In FIG. 2, discussion and explanation may be provided with respect to the above-described example of FIG. 1, and/or with respect to other examples and contexts. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 200 may include module 210 that includes one or more nitric oxide sensors. In some embodiments, a device 102 may include one or more nitric oxide sensors 104. In some embodiments, one or more nitric oxide sensors 104 may detect nitric oxide. In some embodiments, one or more nitric oxide sensors 104 may detect one or more nitric oxide donors. In some embodiments, one or more nitric oxide sensors 104 may detect one or more nitric oxide synthases.

In some embodiments, a device 102 that includes one or more nitric oxide sensors 104 may be configured for implantation into an individual. For example, in some embodiments, a device 102 may be configured for implantation into the genital region of a male individual. In some embodiments, a device 102 may be configured to monitor the nitric oxide concentration in the genital region of a male individual over a series of time points. In some embodiments, such an implanted device 102 may transmit one or more signals 112 that facilitate production of nitric oxide by one or more nitric oxide generators 116 within the genital region of the male. Accordingly, in some embodiments, nitric oxide may be generated to promote erectile function by a male individual.

In some embodiments, one or more devices 102 may include one or more nitric oxide sensors 104 that are configured for placement in association with a wound. For example, in some embodiments, one or more nitric oxide sensors 104 may be configured to detect nitric oxide concentration within and/or on a wound site (e.g., surgical wound, burn, skin lesion, diabetic lesion, etc.). Accordingly, one or more devices 102 may be configured to detect nitric oxide concentration at one or more times and then transmit one or more signals 112 that include information related to the nitric oxide concentration. In some embodiments, the one or more signals 112 may facilitate generation of nitric oxide by one or more nitric oxide generators 116 for application to the wound site. In some embodiments, the one or more signals 112 may indicate that the nitric oxide concentration at the wound site is too low and facilitate generation of nitric oxide by one or more nitric oxide generators 116. In some embodiments, the one or more signals 112 may indicate that the nitric oxide concentration at the wound site is too high and terminate and/or reduce generation of nitric oxide by one or more nitric oxide generators 116. Accordingly, in some embodiments, a device 102 may include one or more nitric oxide sensors 104 that facilitate maintenance of nitric oxide concentration within one or more ranges.

The embodiment 200 may include module 220 that includes one or more transmitters configured to transmit one or more signals that are associated with controlling one or more nitric oxide generators. In some embodiments, a device 102 may include one or more transmitters 106 configured to transmit one or more signals 112 that are associated with controlling one or more nitric oxide generators 116. In some embodiments, one or more transmitters 106 may be configured to transmit one or more signals 112 that include instructions to produce nitric oxide. In some embodiments, one or more transmitters 106 may be configured to transmit one or more signals 112 that include instructions to produce a greater amount of nitric oxide. In some embodiments, one or more transmitters 106 may be configured to transmit one or more signals 112 that include instructions to stop producing nitric oxide. In some embodiments, one or more transmitters 106 may be configured to transmit one or more signals 112 that include instructions to decrease production of nitric oxide. A transmitter 106 may transmit numerous types of signals 112. Examples of signals 112 include, but are not limited to, optical signals 112, radio signals 112, wireless signals 112, hardwired signals 112, infrared signals 112, ultrasonic signals 112, and/or substantially any combination thereof.

Figure 3:
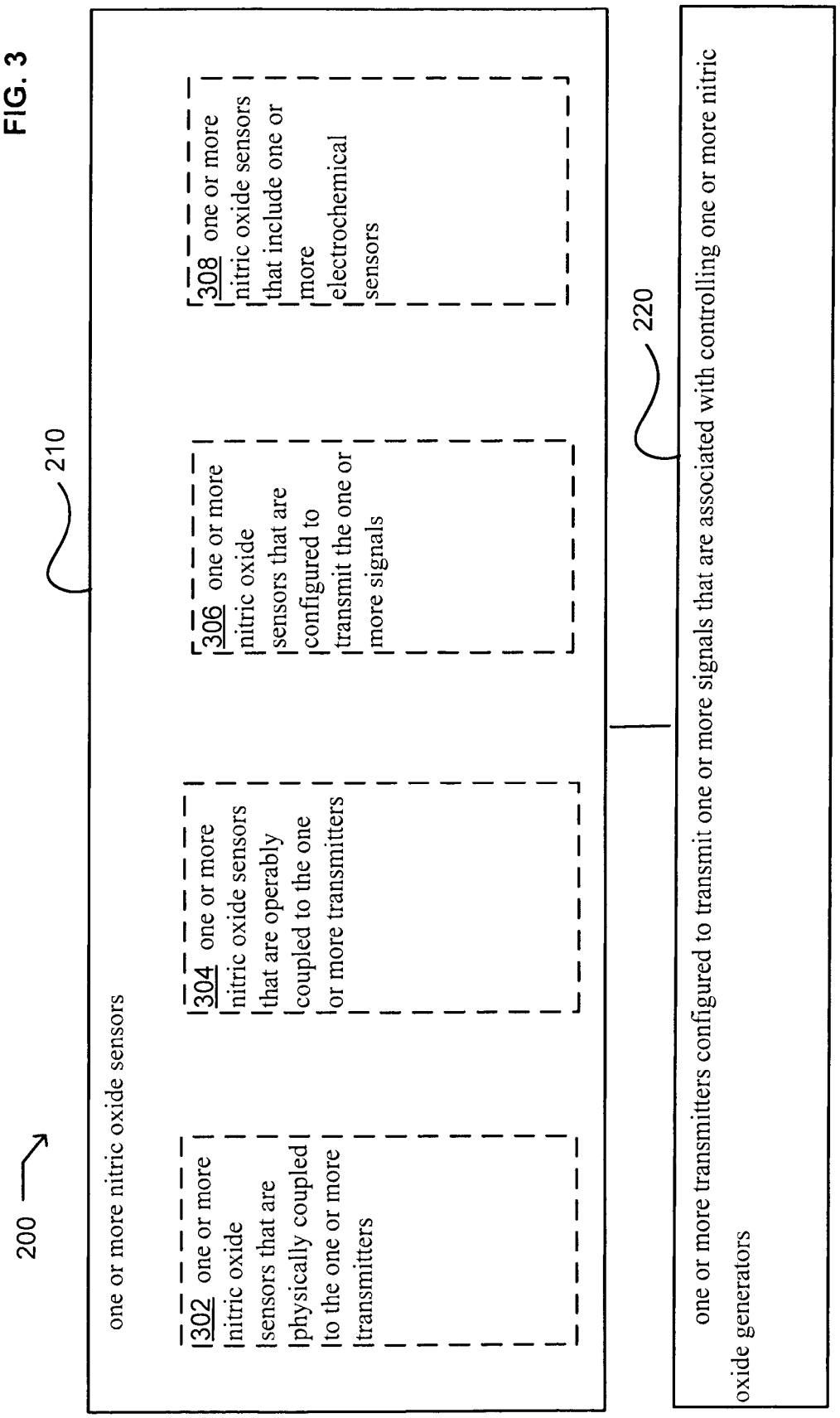
FIG. 3 illustrates alternate embodiments of module 210 of embodiment 200 of device 102 within system 100.

FIG. 3 illustrates alternative embodiments of embodiment 200 of device 102 within system 100 of FIG. 2. FIG. 3 illustrates example embodiments of module 210 of device 102. Additional embodiments may include an embodiment 302, an embodiment 304, an embodiment 306, and/or an embodiment 308.

At embodiment 302, module 210 may include one or more nitric oxide sensors that are physically coupled to the one or more transmitters. In some embodiments, a nitric oxide sensor 104 may include one or more nitric oxide sensors 104 that are physically coupled to one or more transmitters 106. In some embodiments, a device 102 may include one or more nitric oxide sensors 104 that are hardwired to one or more transmitters 106. In some embodiments, the one or more nitric oxide sensors 104 and the one or more transmitters 106 may be linked together into a continuous unit. In some embodiments, the one or more nitric oxide sensors 104 and the one or more transmitters 106 may be separate from each other and physically coupled together through a hardwired connection.

At embodiment 304, module 210 may include one or more nitric oxide sensors that are operably coupled to the one or more transmitters. In some embodiments, a nitric oxide sensor 104 may include one or more nitric oxide sensors 104 that are operably coupled to one or more transmitters 106. In some embodiments, a device 102 may include one or more nitric oxide sensors 104 that are wirelessly connected to one or more transmitters 106. In some embodiments, one or more nitric oxide sensors 104 may be operably connected to one or more transmitters 106 through an intermediate. For example, in some embodiments, one or more nitric oxide sensors 104 may be operably coupled to one or more control units 108 that are operably coupled to one or more transmitters 106. Accordingly, one or more nitric oxide sensors 104 may be operably coupled to one or more transmitters 106 in numerous ways.

At embodiment 306, module 210 may include one or more nitric oxide sensors that are configured to transmit the one or more signals. In some embodiments, a nitric oxide sensor 104 may include one or more nitric oxide sensors 104 that are configured to transmit one or more signals 112. In some embodiments, one or more nitric oxide sensors 104 may include one or more transmitters 106 that may transmit one or more signals 112. For example, in some embodiments, one or more nitric oxide sensors 104 may include one or more transmitters 106 that transmit one or more signals 112 that may be received by one or more receivers 110. Accordingly, in some embodiments, a nitric oxide sensor 104 may transmit one or more signals 112 that are received by receiver 110 and then transmitted by transmitter 106. In some embodiments, two or more nitric oxide sensors 104 may transmit one or more signals 112 that are received by one or more receivers 110 that are associated with device 102 and then the one or more signals 112 may be retransmitted by one or more transmitters 106.

At embodiment 308, module 210 may include one or more nitric oxide sensors that include one or more electrochemical sensors. In some embodiments, a nitric oxide sensor 104 may include one or more nitric oxide sensors 104 that include one or more electrochemical sensors. Nitric oxide sensors 104 may include numerous types of electrochemical sensors. In some embodiments, a nitric oxide specific electrode may include ruthenium and/or at least one oxide of ruthenium. Methods to construct such electrodes are known and have been described (e.g., U.S. Pat. Nos. 6,280,604; 5,980,705). In some embodiments, a nitric oxide sensor 104 may include an amperometric sensor that includes a sensing electrode that is configured to oxidize nitric oxide complexes to generate an electrical current that indicates the concentration of nitric oxide. Methods to construct such electrodes are known and have been described (e.g., U.S. Patent Application No.: 20070181444, Ikeda et al., Sensors, 5:161-170 (2005), Li et al., Electroanalysis, 18:713-718 (2006)). Electrodes that may be used to detect nitric oxide are commercially available (World Precision Instruments, Sarasota, Fla.). In some embodiments, such electrodes may be used to detect nitric oxide at concentrations of about 0.5 nanomolar and above, and may be about 100 micrometers in diameter (World Precision Instruments, Sarasota, Fla.).

Figure 4:
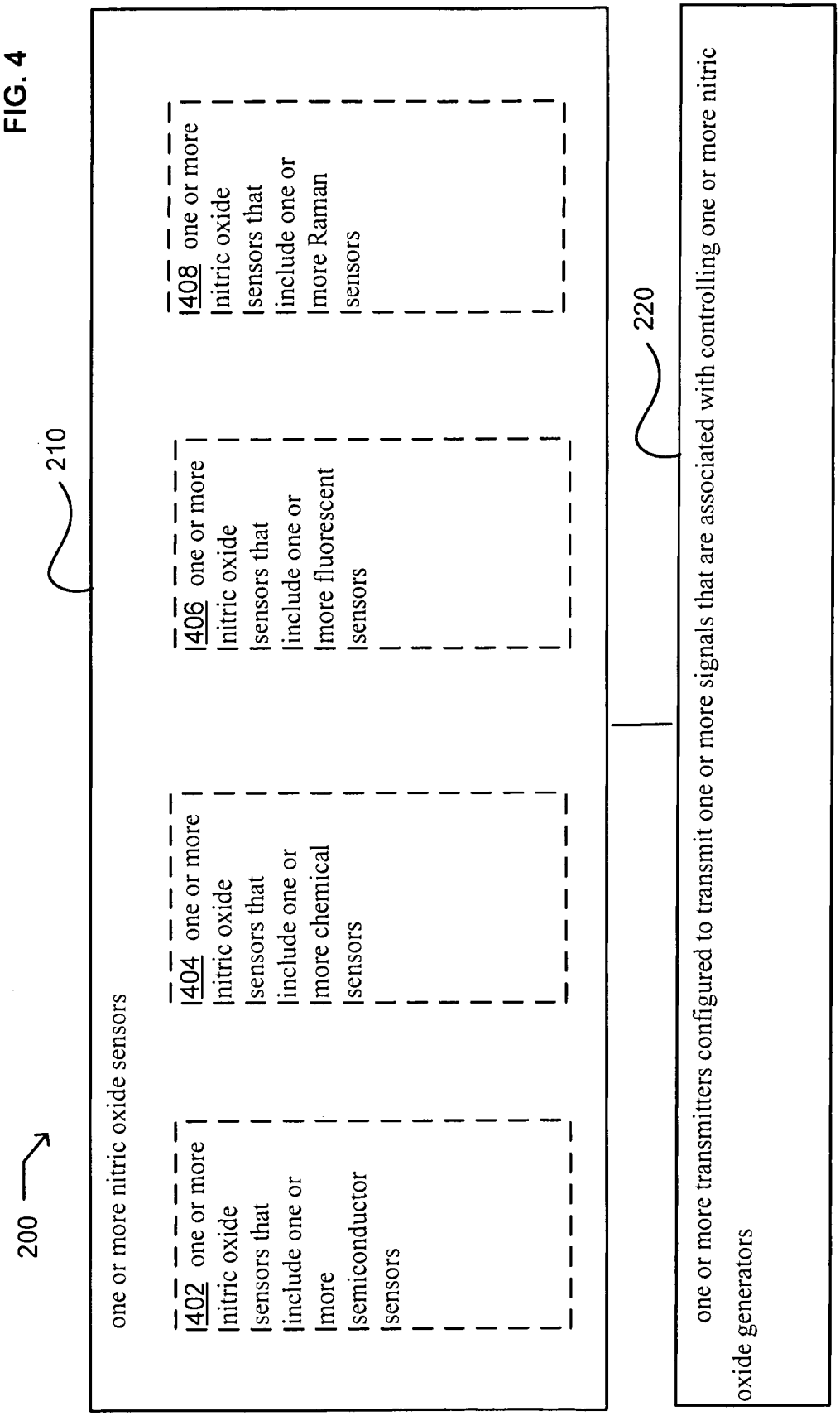
FIG. 4 illustrates alternate embodiments of module 210 of embodiment 200 of device 102 within system 100.

FIG. 4 illustrates alternative embodiments of embodiment 200 of device 102 within system 100 of FIG. 2. FIG. 4 illustrates example embodiments of module 210 of device 102. Additional embodiments may include an embodiment 402, an embodiment 404, an embodiment 406, and/or an embodiment 408.

At embodiment 402, module 210 may include one or more nitric oxide sensors that include one or more semiconductor sensors. In some embodiments, a nitric oxide sensor 104 may include one or more nitric oxide sensors 104 that include one or more semiconductor sensors. In some embodiments, a semiconductor sensor may be a molecular controlled semiconductor resistor of a multilayered GaAs structure to which a layer of multifunctional NO-binding molecules are adsorbed. Such nitric oxide binding molecules may include, but are not limited to, vicinal diamines, metalloporphyrins, metallophthalocyanines, and iron-dithiocarbamate complexes that contain at least one functional group selected from carboxyl, thiol, acyclic sulfide, cyclic disulfide, hydroxamic acid, trichlorosilane or phosphate (e.g., U.S. Published Patent Application No.: 20040072360). In some embodiments, a semiconductive sensor may employ a polycrystalline-oxide semiconductor material that is coated with porous metal electrodes to form a semiconductor sandwich. In some embodiments, the semiconductor material may be formed of $SnO_2$ or ZnO. The porous electrodes may be formed with platinum and used to measure the conductivity of the semiconductor material. In some embodiments, the conductivity of the semiconductor material changes when nitric oxide is absorbed on the surface of the semiconductor material (e.g., U.S. Pat. No. 5,580,433; International Application Publication Number WO 02/057738). One or more nitric oxide sensors 104 may include numerous other types of semiconductor sensors.

At embodiment 404, module 210 may include one or more nitric oxide sensors that include one or more chemical sensors. In some embodiments, a nitric oxide sensor 104 may include one or more nitric oxide sensors 104 that include one or more chemical sensors. For example, in some embodiments, one or more nitric oxide sensors 104 may include one or more chemical sensors that include a reagent solution that undergoes a chemiluminescent reaction with nitric oxide. Accordingly, one or more photodetectors may be used to detect nitric oxide. Methods to construct such detectors are known and have been described (e.g., U.S. Pat. No. 6,100,096). In some embodiments, ozone may be reacted with nitric oxide to produce light in proportion to the amount of nitric oxide present. The light produced may be measured with a photodetector. In some embodiments, nitric oxide sensors 104 may include one or more charge-coupled devices 102 to detect photonic emission.

At embodiment 406, module 210 may include one or more nitric oxide sensors that include one or more fluorescent sensors. In some embodiments, a nitric oxide sensor 104 may include one or more nitric oxide sensors 104 that include one or more fluorescent sensors. In some embodiments, a fluorescent sensor may include one or more fluorescent probes that may be used to detect nitric oxide. For example, in some embodiments, 4,5-diaminofluorescein may be used to determine nitric oxide concentration (e.g., Rathel et al., Biol. Proced. Online, 5:136-142 (2003)). Probes that may be used to detect nitric oxide are commercially available (EMD Chemicals Inc., San Diego, Calif.).

At embodiment 408, module 210 may include one or more nitric oxide sensors that include one or more Raman sensors. In some embodiments, a nitric oxide sensor 104 may include one or more nitric oxide sensors 104 that include one or more Raman sensors. Methods to use Raman spectroscopy to detect nitric oxide are known and have been described (e.g., U.S. Patent Application No.: 20060074282). In addition, Raman spectrometers are commercially available (e.g., Raman Systems, Austin, Tex. and B&W Tek, Inc., Newark, Del.).

Figure 5:
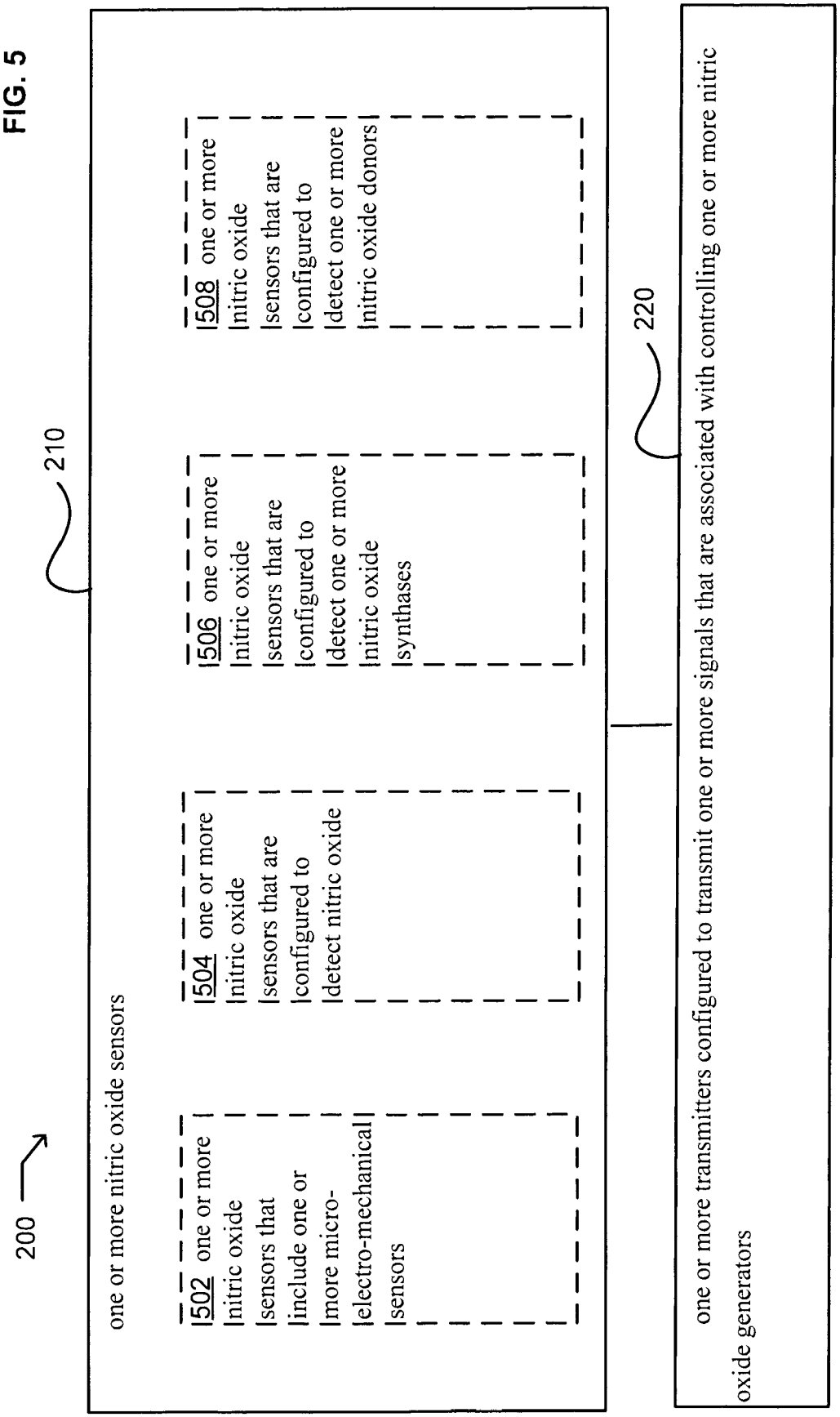
FIG. 5 illustrates alternate embodiments of module 210 of embodiment 200 of device 102 within system 100.

FIG. 5 illustrates alternative embodiments of embodiment 200 of device 102 within system 100 of FIG. 2. FIG. 5 illustrates example embodiments of module 210 of device 102. Additional embodiments may include an embodiment 502, an embodiment 504, an embodiment 506, and/or an embodiment 508.

At embodiment 502, module 210 may include one or more nitric oxide sensors that include one or more micro-electro-mechanical sensors. In some embodiments, a nitric oxide sensor 104 may include one or more nitric oxide sensors 104 that include one or more micro-electro-mechanical sensors. In some embodiments, micro-electro-mechanical systems may be used to detect nitric oxide synthase. In some embodiments, antibodies and/or aptamers that bind to nitric oxide synthase may be used within one or more micro-electro-mechanical systems to detect nitric oxide synthase. Methods to construct micro-electro-mechanical detectors have been described (e.g., Gau et al., Biosensors & Bioelectronics, 16:745-755 (2001)). Accordingly, nitric oxide sensors 104 may be configured in numerous ways to detect one or more nitric oxide synthases.

At embodiment 504, module 210 may include one or more nitric oxide sensors that are configured to detect nitric oxide. In some embodiments, a nitric oxide sensor 104 may include one or more nitric oxide sensors 104 that are configured to detect nitric oxide. In some embodiments, a nitric oxide sensor 104 that is configured to detect nitric oxide may be configured for use on the outside surface of an individual. For example, in some embodiments, one or more nitric oxide sensors 104 may be configured to detect the concentration of nitric oxide on the surface of skin, a wound, and the like. In some embodiments, a nitric oxide sensor 104 may be configured to utilize fluorescence to detect nitric oxide. For example, in some embodiments, a nitric oxide sensor 104 may detect nitric oxide through use of one or more fluorescent probes, such as 4,5-diaminofluorescein diacetate (EMD Chemicals Inc., San Diego, Calif.). In some embodiments, a nitric oxide sensor 104 may detect nitric oxide through use of one or more electrodes. For example, in some embodiments, a nitric oxide sensor 104 may utilize an electrode that includes a single walled carbon nanotube and an ionic liquid to detect nitric oxide (e.g., Li et al., Electroanalysis, 18:713-718 (2006)). Nitric oxide sensors 104 are commercially available and have been described (e.g., World Precision Instruments, Inc., Sarasota, Fla., USA; U.S. Pat. Nos. 6,100,096; 6,280,604; 5,980,705).

At embodiment 506, module 210 may include one or more nitric oxide sensors that are configured to detect one or more nitric oxide synthases. In some embodiments, a nitric oxide sensor 104 may include one or more nitric oxide sensors 104 that are configured to detect one or more nitric oxide synthases. In some embodiments, one or more nitric oxide sensors 104 may be configured to detect nitric oxide synthase activity. Nitric oxide synthase detection kits are commercially available (e.g., Cell Technology, Inc., Mountain View, Calif.). In some embodiments, one or more nitric oxide sensors 104 may be configured to detect nitric oxide synthase messenger ribonucleic acid (mRNA). Methods that may be used to detect such mRNA have been reported (e.g., Sonoki et al., Leukemia, 13:713-718 (1999)). In some embodiments, one or more nitric oxide sensors 104 may be configured to detect nitric oxide synthase through immunological methods. Methods that may be used to detect nitric oxide synthase directly been reported (e.g., Burrell et al., J. Histochem. Cytochem., 44:339-346 (1996) and Hattenbach et al., Ophthalmologica, 216:209-214 (2002)). In some embodiments, micro-electro-mechanical systems may be used to detect nitric oxide synthase. In some embodiments, antibodies and/or aptamers that bind to nitric oxide synthase may be used within one or more micro-electro-mechanical systems to detect nitric oxide synthase. Methods to construct micro-electro-mechanical detectors have been described (e.g., Gau et al., Biosensors & Bioelectronics, 16:745-755 (2001)). Accordingly, nitric oxide sensors 104 may be configured in numerous ways to detect one or more nitric oxide synthases.

At embodiment 508, module 210 may include one or more nitric oxide sensors that are configured to detect one or more nitric oxide donors. In some embodiments, a nitric oxide sensor 104 may include one or more nitric oxide sensors 104 that are configured to detect one or more nitric oxide donors. In some embodiments, one or more nitric oxide sensors 104 may include one or more surface plasmon resonance chemical electrodes that are configured to detect one or more nitric oxide donors. For example, in some embodiments, one or more nitric oxide sensors 104 may include one or more surface plasmon resonance chemical electrodes that include antibodies and/or aptamers that bind to one or more nitric oxide donors. Accordingly, such electrodes may be used to detect the one or more nitric oxide donors through use of surface plasmon resonance. Methods to construct surface plasmon resonance chemical electrodes are known and have been described (e.g., U.S. Pat. No. 5,858,799; Lin et al., Applied Optics, 46:800-806 (2007)). In some embodiments, antibodies and/or aptamers that bind to one or more nitric oxide donors may be used within one or more micro-electro-mechanical systems to detect one or more nitric oxide donors. Methods to construct micro-electro-mechanical detectors have been described (e.g., Gau et al., Biosensors & Bioelectronics, 16:745-755 (2001)).

Figure 6:
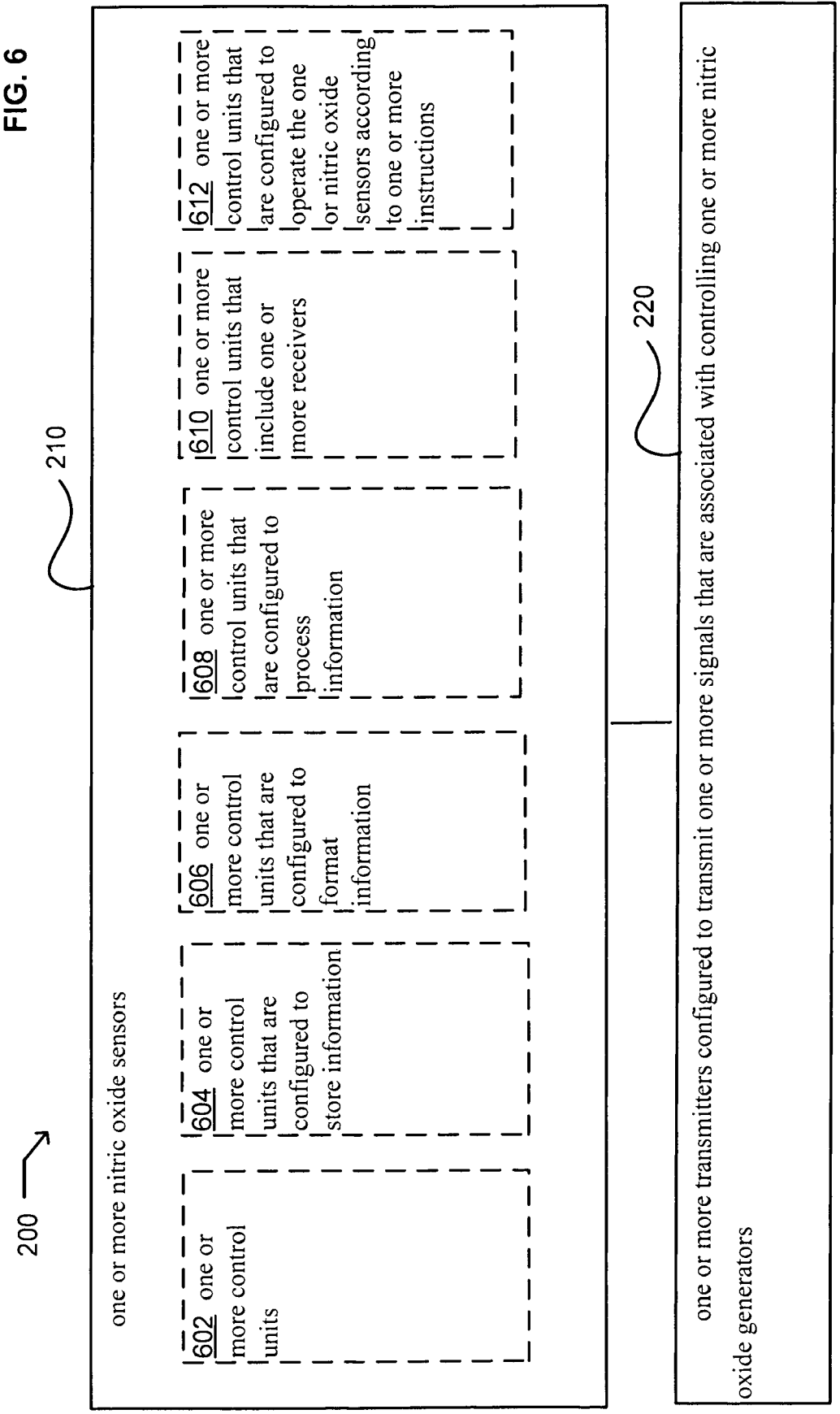
FIG. 6 illustrates alternate embodiments of module 210 of embodiment 200 of device 102 within system 100.

FIG. 6 illustrates alternative embodiments of embodiment 200 of device 102 within system 100 of FIG. 2. FIG. 6 illustrates example embodiments of module 210 of device 102. Additional embodiments may include an embodiment 602, an embodiment 604, an embodiment 606, an embodiment 608, an embodiment 610, and/or an embodiment 612.

At embodiment 602, module 210 may include one or more control units. In some embodiments, a nitric oxide sensor 104 may include one or more nitric oxide sensors 104 that include one or more control units 108. In some embodiments, one or more nitric oxide sensors 104 may be operably associated with one or more control units 108 through a hardwired connection. In some embodiments, one or more nitric oxide sensors 104 may be operably associated with one or more control units 108 through a wireless connection. In some embodiments, one or more nitric oxide sensors 104 may be configured to send one or more signals to one or more control units 108. In some embodiments, one or more nitric oxide sensors 104 may be configured to receive one or more signals 112 from one or more control units 108.

At embodiment 604, module 210 may include one or more control units that are configured to store information. In some embodiments, a nitric oxide sensor 104 may include one or more nitric oxide sensors 104 that include one or more control units 108 that are configured to store information. In some embodiments, one or control units 108 may include memory that is configured to store information. In some embodiments, one or control units 108 may store information that includes operating instructions for one or more nitric oxide sensors 104. For example, in some embodiments, information may include instructions for one or more nitric oxide sensors 104 to operate at one or more times. In some embodiments, information may include instructions for one or more nitric oxide sensors 104 to operate for certain periods of time. For example, in some embodiments, one or more nitric oxide sensors 104 may be instructed to operate for a period of time (e.g., thirty seconds) and then stop operating for a period of time. Accordingly, in some embodiments, one or more nitric oxide sensors 104 may be instructed with regard to when to operate and for the period of time to operate. One or more control units 108 may be configured to store numerous types of information. In some embodiments, one or more control units 108 may be configured to store programs. In some embodiments, one or more control units 108 may be configured to store programs that may be used to control the operation of one or more nitric oxide sensors 104 in a manner that is response to input. For example, in some embodiments, one or more control units 108 may be responsive to one or more signals associated with one or more nitric oxide generators 116.

At embodiment 606, module 210 may include one or more control units that are configured to format information. In some embodiments, a nitric oxide sensor 104 may include one or more nitric oxide sensors 104 that include one or more control units 108 that are configured to format information. In some embodiments, one or more control units 108 may be configured to format information in a manner such that the information may be transmitted. In some embodiments, one or more control units 108 may formation information such that it may be used to control the operation of one or more nitric oxide sensors 104.

At embodiment 608, module 210 may include one or more control units that are configured to process information. In some embodiments, a nitric oxide sensor 104 may include one or more nitric oxide sensors 104 that include one or more control units 108 that are configured to process information. In some embodiments, one or more control units 108 may be configured to process information associated with one or more nitric oxide generators 116. For example, in some embodiments, one or more control units 108 may receive information with regard to nitric oxide generated by one or more nitric oxide generators 116. In some embodiments, such information may be used to adjust the sensitivity of one or more nitric oxide sensors 104. In some embodiments, such information may be used to adjust one or more time periods when one or more nitric oxide sensors 104 operate. Accordingly, in some embodiments, such information may be used to couple the operation of one or more nitric oxide generators 116 to the operation of one or more nitric oxide sensors 104.

At embodiment 610, module 210 may include one or more control units that include one or more receivers. In some embodiments, a nitric oxide sensor 104 may include one or more nitric oxide sensors 104 that include one or more control units 108 that include one or more receivers 110. In some embodiments, one or more control units 108 may include one or more receivers 110 that are configured to receive one or more remote signals 122. In some embodiments, one or more control units 108 may include one or more receivers 110 that are configured to receive one or more information packets. In some embodiments, one or more control units 108 may include one or more receivers 110 that are configured to receive one or more remote signals 122 that are associated with one or more nitric oxide generators 116. In some embodiments, one or more control units 108 may include one or more receivers 110 that are configured to receive one or more remote signals 122 that are associated with user input. In some embodiments, one or more control units 108 may include one or more receivers 110 that are configured to receive one or more signals 112 from one or more transmitters 106 that are associated with device 102.

At embodiment 612, module 210 may include one or more control units that are configured to operate the one or nitric oxide sensors according to one or more instructions. In some embodiments, a nitric oxide sensor 104 may include one or more control units 108 that are configured to operate the one or nitric oxide sensors 104 according to one or more instructions. In some embodiments, one or more control units 108 may be configured to operate one or more nitric oxide sensors 104 according to one or more instructions received from one or more processing units. In some embodiments, one or more control units 108 may be configured to operate one or more nitric oxide sensors 104 according to one or more instructions received from one or more user interfaces 124. Accordingly, one or more control units 108 may receive numerous instructions.

Figure 7:
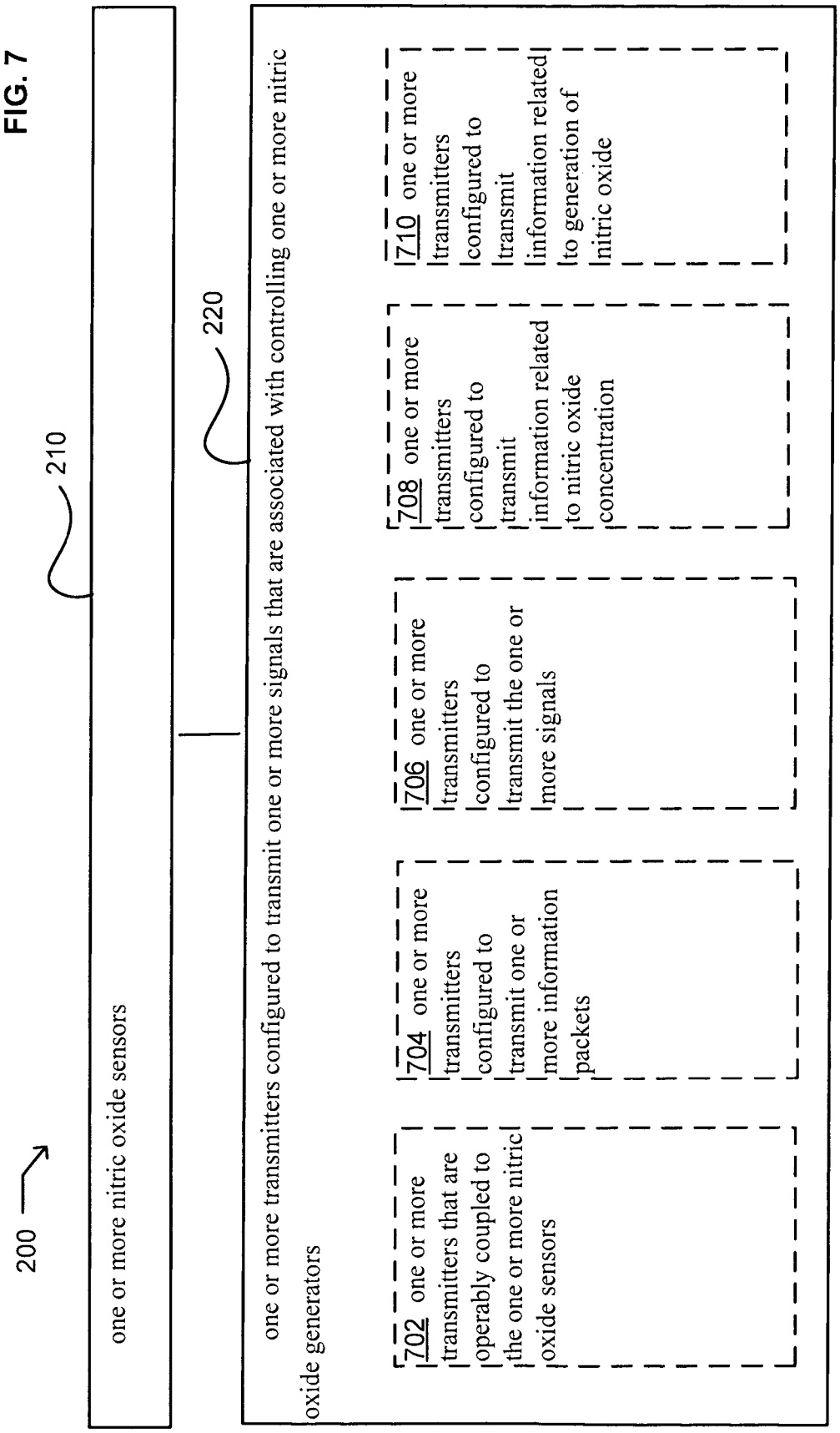
FIG. 7 illustrates alternate embodiments of module 220 of embodiment 200 of device 102 within system 100.

FIG. 7 illustrates alternative embodiments of embodiment 200 of device 102 within system 100 of FIG. 2. FIG. 7 illustrates example embodiments of module 220 of device 102. Additional embodiments may include an embodiment 702, an embodiment 704, an embodiment 706, an embodiment 708, and/or an embodiment 710.

At embodiment 702, module 220 may include one or more transmitters that are operably coupled to the one or more nitric oxide sensors. In some embodiments, a transmitter 106 may include one or more transmitters 106 that include one or more transmitters 106 that are operably coupled to one or more nitric oxide sensors 104. In some embodiments, one or more transmitters 106 may be directly coupled to one or more nitric oxide sensors 104 to form a single unit. In some embodiments, one or more transmitters 106 may be operably coupled to one or more nitric oxide sensors 104 through a hardwired connection. In some embodiments, one or more transmitters 106 may be directly coupled to one or more nitric oxide sensors 104 through a wireless connection. Accordingly, in some embodiments, one or more transmitters 106 may be physically separated from one or more nitric oxide sensors 104.

At embodiment 704, module 220 may include one or more transmitters configured to transmit one or more information packets. In some embodiments, a transmitter 106 may include one or more transmitters 106 that include one or more transmitters 106 configured to transmit one or more information packets. For example, in some embodiments, one or more transmitters 106 may gather information from one or more nitric oxide sensors 104 over a period of time and then transmit the information in one or more information packets. In some embodiments, one or more transmitters 106 may be configured to transmit one or more information packets for receipt by one or more nitric oxide generators 116. In some embodiments, one or more transmitters 106 may be configured to transmit one or more information packets for receipt by one or more processing units 118. In some embodiments, one or more transmitters 106 may be configured to transmit one or more information packets for receipt by one or more user interfaces 124.

At embodiment 706, module 220 may include one or more transmitters configured to transmit the one or more signals. In some embodiments, a transmitter 106 may include one or more transmitters 106 that include one or more transmitters 106 configured to transmit one or more signals 112. One or more transmitters 106 may be configured to transmit numerous types of signals 112. Examples of such signals 112 include, but are not limited to, optical signals 112, radio signals 112, wireless signals 112, hardwired signals 112, infrared signals 112, ultrasonic signals 112, and the like (e.g., U.S. Pat. Nos. RE39,785; 7,260,768; 7,260,764; 7,260,402; 7,257,327; 7,215,887; 7,218,900; herein incorporated by reference). In some embodiments, one or more transmitters 106 may transmit one or more signals 112 that are encrypted. Numerous types of transmitters are known and have been described (e.g., U.S. Pat. Nos. and Published U.S. Patent Application: 7,236,595; 7,260,155; 7,227,956; US2006/0280307; herein incorporated by reference).

At embodiment 708, module 220 may include one or more transmitters configured to transmit information related to nitric oxide concentration. In some embodiments, a transmitter 106 may include one or more transmitters 106 that include one or more transmitters 106 configured to transmit information related to nitric oxide concentration. In some embodiments, one or more transmitters 106 may be configured to transmit information related to the concentration of nitric oxide at a single time point. For example, in some embodiments, one or more transmitters 106 may be configured to transmit one or more nitric oxide concentrations to one or more processing units 118 upon being detected. In some embodiments, one or more transmitters 106 may be configured to transmit one or more signals 112 that include information associated with one or more nitric oxide concentrations to one or more nitric oxide generators 116 upon being detected. In some embodiments, one or more transmitters 106 may be configured to transmit one or more signals 112 that include information associated with one or more nitric oxide concentrations to one or more processing units 118 upon being detected. In some embodiments, such transmitters 106 may be used within a feedback system to cause the nitric oxide concentration within a space and/or tissue to reach and/or be maintained at a selected concentration. In some embodiments, one or more transmitters 106 may transmit information related to changes in nitric oxide concentration. For example, in some embodiments, one or more transmitters 106 may transmit information related to a change in nitric oxide concentration over a time period. Accordingly, one or more transmitters 106 may be configured in numerous ways.

At embodiment 710, module 220 may include one or more transmitters configured to transmit information related to generation of nitric oxide. In some embodiments, a transmitter 106 may include one or more transmitters 106 that include one or more transmitters 106 configured to transmit information related to generation of nitric oxide. For example, in some embodiments, one or more transmitters 106 may transmit one or more signals 112 that include one or more instructions for one or more nitric oxide generators 116 to generate nitric oxide. In some embodiments, one or more transmitters 106 may transmit one or more signals 112 that include one or more instructions for one or more nitric oxide generators 116 to stop generating nitric oxide. In some embodiments, one or more transmitters 106 may transmit one or more signals 112 that include one or more instructions for one or more nitric oxide generators 116 to generate nitric oxide at a greater rate. In some embodiments, one or more transmitters 106 may transmit one or more signals 112 that include one or more instructions for one or more nitric oxide generators 116 to generate nitric oxide at a slower rate. Accordingly, one or more transmitters 106 may be configured in numerous ways.

Figure 8:
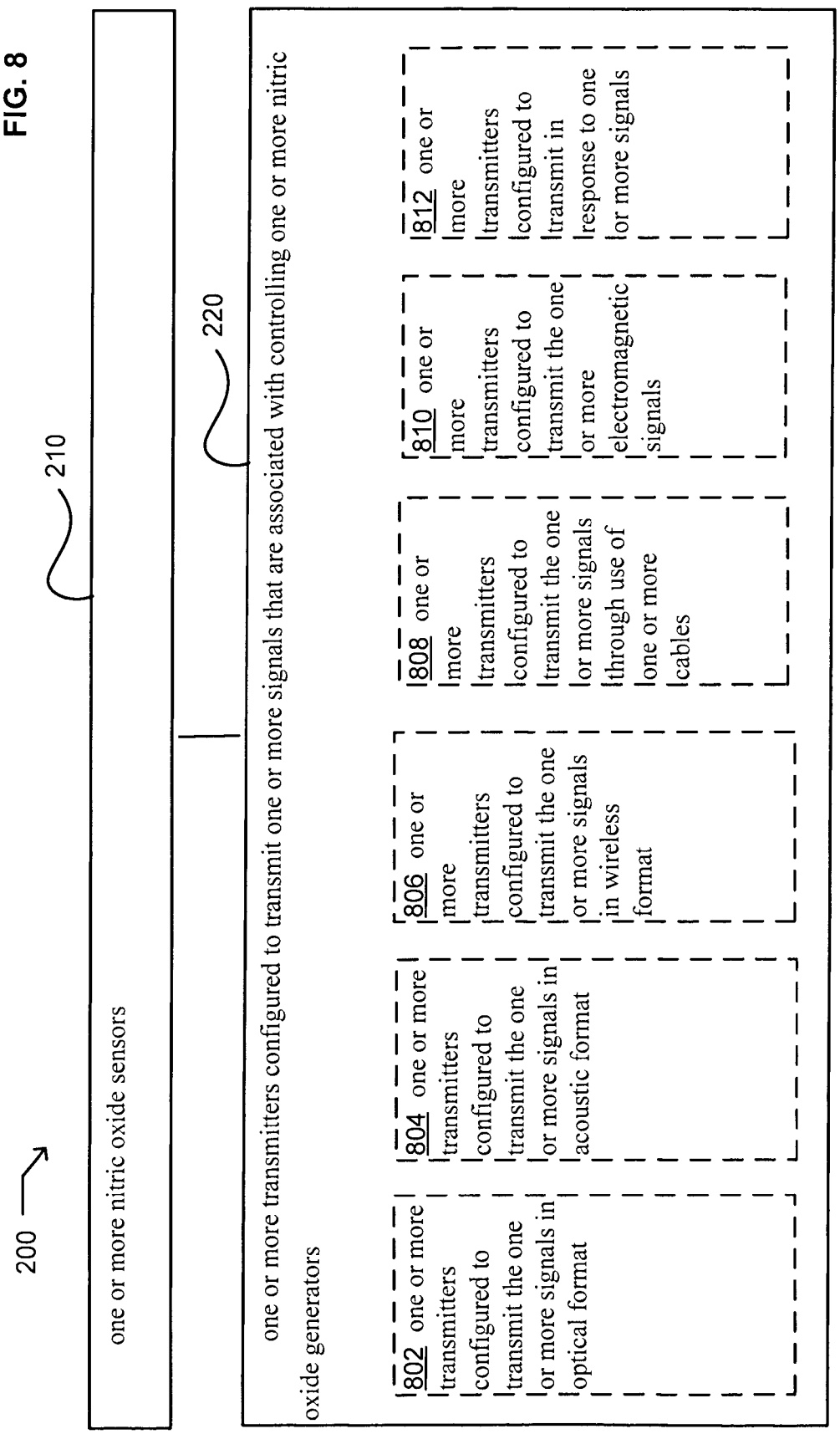
FIG. 8 illustrates alternate embodiments of module 220 of embodiment 200 of device 102 within system 100.

FIG. 8 illustrates alternative embodiments of embodiment 200 of device 102 within system 100 of FIG. 2. FIG. 8 illustrates example embodiments of module 220 of device 102. Additional embodiments may include an embodiment 802, an embodiment 804, an embodiment 806, an embodiment 808, an embodiment 810, and/or an embodiment 812.

At embodiment 802, module 220 may include one or more transmitters configured to transmit the one or more signals in optical format. In some embodiments, a transmitter 106 may include one or more transmitters 106 that include one or more transmitters 106 configured to transmit one or more signals 112 in optical format (e.g., U.S. Pat. No. 7,298,977). In some embodiments, an optical transmitter 106 may receive an input that is processed into an optical signal 112 and transmitted through use of an optical transmission medium. In some embodiments, a transmitter 106 may include a light emitting diode. In some embodiments, a transmitter 106 may include an injection laser diode.

At embodiment 804, module 220 may include one or more transmitters configured to transmit the one or more signals in acoustic format. In some embodiments, a transmitter 106 may include one or more transmitters 106 that include one or more transmitters 106 configured to transmit one or more signals 112 in acoustic format. An acoustic transmitter 106 may include nearly any transmitter 106 that can transmit acoustic energy. In some embodiments, an acoustic transmitter 106 may include a signal generator, an amplifier, and a speaker. In some embodiments, an acoustic transmitter 106 may include a tuning fork, a tone generator, or the like. Examples of acoustic transmitters have been described (e.g., U.S. Pat. Nos. 7,220,258; 7,261,693).

At embodiment 806, module 220 may include one or more transmitters configured to transmit the one or more signals in wireless format. In some embodiments, a transmitter 106 may include one or more transmitters 106 that include one or more transmitters 106 configured to transmit one or more signals 112 in wireless format. In some embodiments, one or more transmitters 106 may be FM transmitters 106. In some embodiments, one or more transmitters 106 may be Rf transmitters 106. In some embodiments, one or more transmitters 106 may be infrared transmitters 106. Wireless transmitters have been described and are commercially available (e.g., U.S. Pat. Nos. 7,280,811; 7,181,174).

At embodiment 808, module 220 may include one or more transmitters configured to transmit the one or more signals through use of one or more cables. In some embodiments, a transmitter 106 may include one or more transmitters 106 that include one or more transmitters 106 configured to transmit one or more signals 112 through use of one or more cables. One or more transmitters 106 may be configured to transmit one or more signals 112 using numerous types of cable. Examples of such cable include, but are not limited to, analog cables, digital cables, coaxial cables, optical cables, and the like.

At embodiment 810, module 220 may include one or more transmitters configured to transmit one or more electromagnetic signals. In some embodiments, a transmitter 106 may include one or more transmitters 106 that include one or more transmitters 106 configured to transmit one or more electromagnetic signals 112. Examples of electromagnetic signals 112 include, but are not limited to, visible light, infrared light, ultraviolet light, radio waves, microwaves, terahertz radiation, and the light.

At embodiment 812, module 220 may include one or more transmitters configured to transmit in response to one or more signals. In some embodiments, a transmitter 106 may include one or more transmitters 106 that include one or more transmitters 106 configured to transmit one or more signals 112 in response to one or more remote signals 122. In some embodiments, one or more transmitters 106 may transmit one or more signals 112 in response to receipt of one or more remote signals 122 associated with one or more nitric oxide generators 116. In some embodiments, one or more transmitters 106 may transmit one or more signals 112 in response to receipt of one or more remote signals 122 associated with one or more user interfaces 124. In some embodiments, one or more transmitters 106 may transmit one or more signals 112 in response to receipt of one or more remote signals 122 associated with one or more processing units 118. For example, in some embodiments, one or more transmitters 106 may receive one or more remote signals 122 from one or more processing units 118 requesting information related to nitric oxide concentration. Accordingly, one or more transmitters 106 may transmit one or more information packets in response to receipt of the one or more remote signals 122. One or more transmitters 106 may be configured to transmit one or more signals 112 and/or information packets in response to receipt of numerous remote signals 122.

Figure 9:
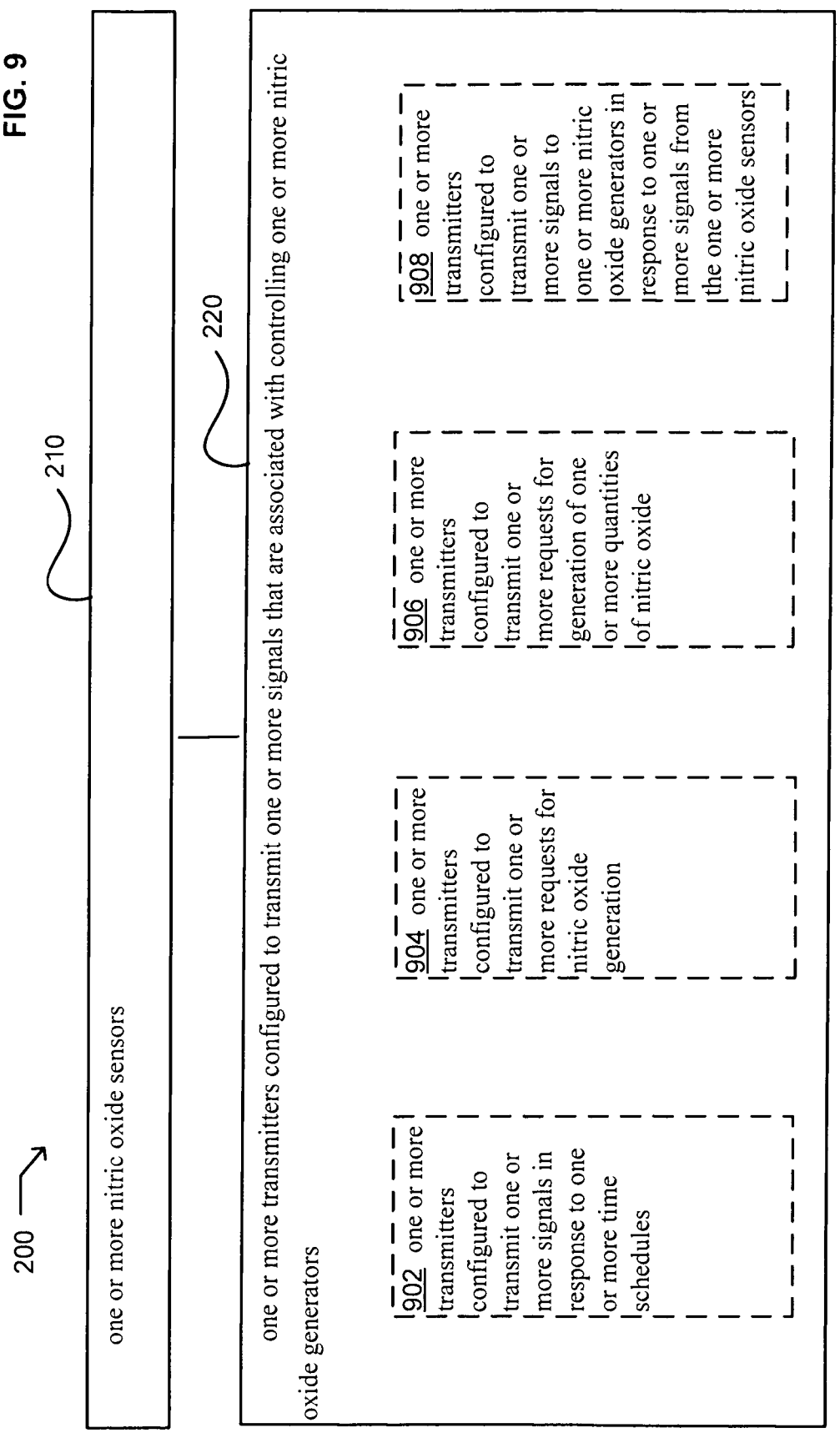
FIG. 9 illustrates a partial view of a system 900 that includes a computer program for executing a computer process on a computing device.

FIG. 9 illustrates alternative embodiments of embodiment 200 of device 102 within system 100 of FIG. 2. FIG. 9 illustrates example embodiments of module 220 of device 102. Additional embodiments may include an embodiment 902, an embodiment 904, an embodiment 906, and/or an embodiment 908.

At embodiment 902, module 220 may include one or more transmitters configured to transmit one or more signals in response to one or more time schedules. In some embodiments, a transmitter 106 may include one or more transmitters 106 configured to transmit one or more signals 112 in response to one or more time schedules. In some embodiments, one or more transmitters 106 may transmit one or more signals 112 at one or more selected times. For example, in some embodiments, one or more transmitters 106 may transmit one or more signals 112 at a selected clock time (e.g., 9:45 PM). In some embodiments, one or more transmitters 106 may transmit one or more signals 112 after a selected amount of time (e.g., 20 minutes).

At embodiment 904, module 220 may include one or more transmitters configured to transmit one or more requests for nitric oxide generation. In some embodiments, a transmitter 106 may include one or more transmitters 106 configured to transmit one or more requests for nitric oxide generation. For example, in some embodiments, one or more transmitters 106 may be configured to transmit one or more signals 112 that may facilitate generation by one or more nitric oxide generators 116.

At embodiment 906, module 220 may include one or more transmitters configured to transmit one or more requests for generation of one or more quantities of nitric oxide. In some embodiments, a transmitter 106 may include one or more transmitters 106 configured to transmit one or more requests for generation of one or more quantities of nitric oxide. For example, in some embodiments, one or more transmitters 106 may be configured to transmit one or more signals 112 that may facilitate generation of a certain amount of nitric oxide by one or more nitric oxide generators 116.

At embodiment 908, module 220 may include one or more transmitters configured to transmit one or more signals to one or more nitric oxide generators in response to one or more signals from the one or more nitric oxide sensors. In some embodiments, a transmitter 106 may include one or more transmitters 106 configured to transmit one or more signals 112 to one or more nitric oxide generators 116 in response to the one or more nitric oxide sensors 104. For example, in some embodiments, one or more nitric oxide sensors 104 may detect that nitric oxide concentration is low and one or more transmitters 106 may respond by transmitting one or more signals 112 to which one or more nitric oxide generators 116 respond by generating nitric oxide. In some embodiments, one or more nitric oxide sensors 104 may detect that nitric oxide concentration is high and one or more transmitters 106 may respond by transmitting one or more signals 112 to which one or more nitric oxide generators 116 respond by halting generation of nitric oxide.

Figure 10:
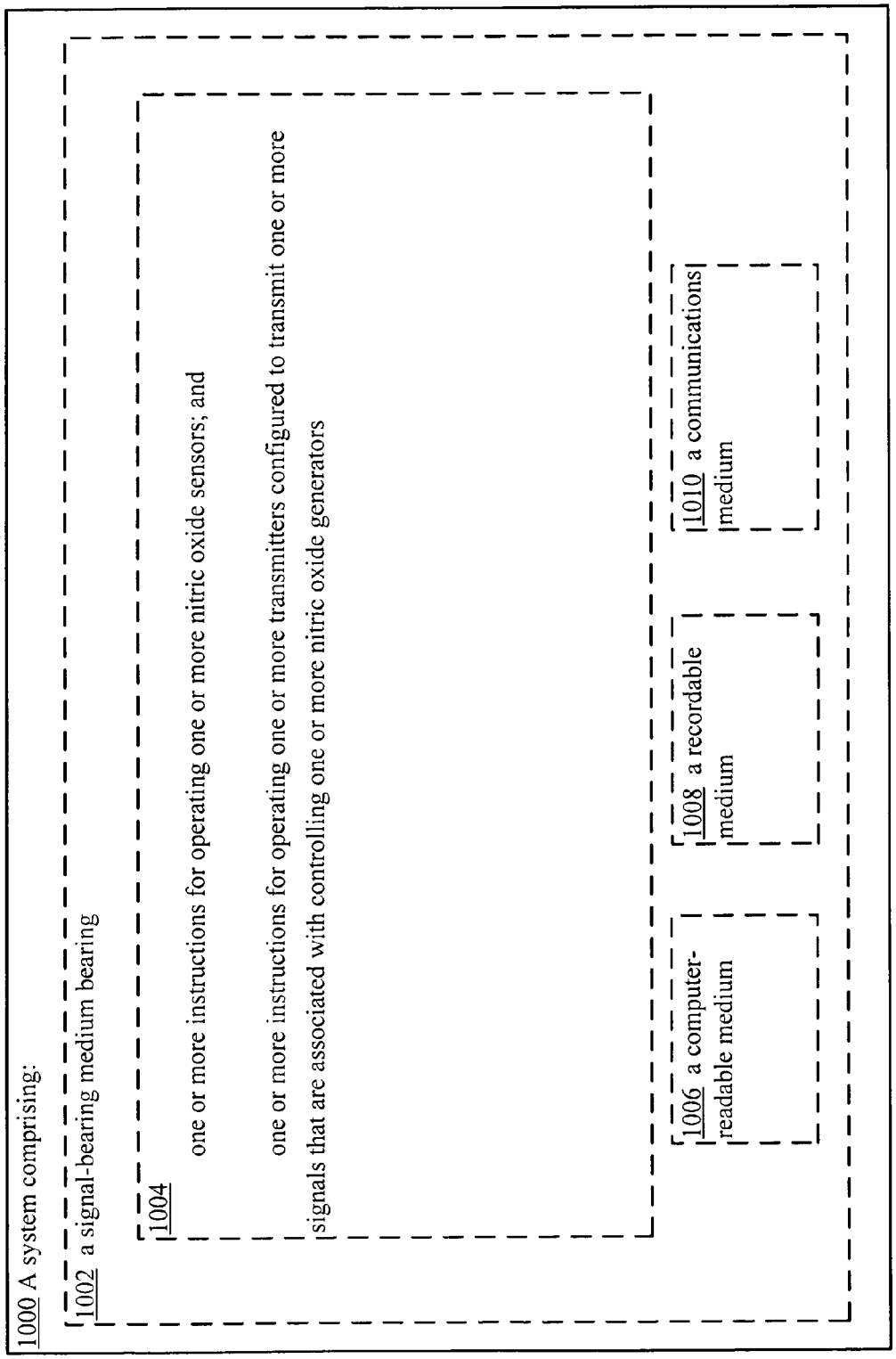
FIG. 10 illustrates a partial view of a system 1000 that includes a computer program for executing a computer process on a computing device.

FIG. 10 illustrates a partial view of a system 1000 that includes a computer program 1004 for executing a computer process on a computing device. An embodiment of system 1000 is provided using a signal-bearing medium 1002 bearing one or more instructions for operating one or more nitric oxide sensors 104 and one or more instructions for operating one or more transmitters 106 configured to transmit one or more signals 112 that are associated with controlling one or more nitric oxide generators 116. The one or more instructions may be, for example, computer executable and/or logic-implemented instructions. In some embodiments, the signal-bearing medium 1002 may include a computer-readable medium 1006. In some embodiments, the signal-bearing medium 1002 may include a recordable medium 1008. In some embodiments, the signal-bearing medium 1002 may include a communications medium 1010.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity (e.g., such as Sprint, Cingular, Nextel, etc.), etc.

Although the user interface 124 is shown/described herein as a single illustrated figure that is associated with an individual, those skilled in the art will appreciate that a user interface 124 may be utilized by a user 126 that is a representative of a human user 126, a robotic user 126 (e.g., computational entity), and/or substantially any combination thereof (e.g., a user 126 may be assisted by one or more robotic based systems). In addition, a user 126 as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A system for generating nitric oxide from one or more photolyzable nitric oxide donors comprising:
   one or more sensors configured to detect nitric oxide;
   one or more transmitters;
   one or more controllers configured to receive one or more signals of at least one of the one or more sensors and to transmit using at least one of the one or more transmitters one or more signals; and
   one or more light sources configured to facilitate release of nitric oxide from at least one of the one or more photolyzable nitric oxide donors in response to at least one of the one or more signals of the one or more controllers.

2. The system of claim 1, wherein the one or more sensors configured to detect nitric oxide comprises:
   one or more semiconductor sensors configured to detect nitric oxide.

3. The system of claim 1, wherein the one or more sensors configured to detect nitric oxide comprises:
   one or more electrochemical sensors configured to detect nitric oxide.

4. The system of claim 1, wherein the one or more sensors configured to detect nitric oxide comprises:

one or more chemical sensors configured to detect nitric oxide.

5. The system of claim 1, wherein the one or more sensors configured to detect nitric oxide comprises:
one or more fluorescent sensors configured to detect nitric oxide.

6. The system of claim 1, wherein the one or more sensors configured to detect nitric oxide comprises:
one or more Raman sensors configured to detect nitric oxide.

7. The system of claim 1, wherein the one or more sensors configured to detect nitric oxide comprises:
one or more electro-mechanical sensors configured to detect nitric oxide.

8. The system of claim 1, wherein the one or more sensors configured to detect nitric oxide comprises:
one or more nitric oxide specific sensors configured to detect nitric oxide.

9. The system of claim 1, wherein the one or more sensors configured to detect nitric oxide comprises:
one or more sensors configured to detect nitric oxide at one or more surfaces.

10. The system of claim 1, wherein the one or more sensors configured to detect nitric oxide comprises:
one or more sensors configured to detect nitric oxide in vivo.

11. The system of claim 1, wherein the one or more sensors configured to detect nitric oxide comprises:
one or more implantable sensors configured to detect nitric oxide.

12. The system of claim 1, wherein the one or more sensors configured to detect nitric oxide comprises:
one or more sensors configured to detect nitric oxide within one or more spaces.

13. The system of claim 1, wherein the one or more sensors configured to detect nitric oxide comprises:
one or more sensors configured to monitor nitric oxide over a series of time points.

14. The system of claim 1, further comprising:
one or more sensors configured to detect one or more nitric oxide synthases.

15. The system of claim 1, further comprising:
one or more sensors configured to detect one or more nitric oxide donors.

16. The system of claim 1, wherein the one or more controllers configured to receive one or more signals of at least one of the one or more sensors and to transmit using at least one of the one or more transmitters one or more signals comprises:
one or more controllers configured to process information.

17. The system of claim 1, wherein the one or more controllers configured to receive one or more signals of at least one of the one or more sensors and to transmit using at least one of the one or more transmitters one or more signals comprises:
one or more controllers configured to receive user input.

18. The system of claim 1, wherein the one or more controllers configured to receive one or more signals of at least one of the one or more sensors and to transmit using at least one of the one or more transmitters one or more signals comprises:
one or more controllers configured to operate at least one of the one or more sensors in accordance with one or more instructions.

19. The system of claim 1, wherein the one or more controllers configured to receive one or more signals of at least one of the one or more sensors and to transmit using at least one of the one or more transmitters one or more signals comprises:
one or more controllers configured to operate at least one of the one or more sensors in response to input.

20. The system of claim 1, wherein the one or more controllers configured to receive one or more signals of at least one of the one or more sensors and to transmit using at least one of the one or more transmitters one or more signals comprises:
one or more controllers configured to regulate operation time and/or sensitivity of at least one of the one or more sensors.

21. The system of claim 1, wherein the one or more controllers configured to receive one or more signals of at least one of the one or more sensors and to transmit using at least one of the one or more transmitters one or more signals comprises:
one or more controllers configured to receive one or more signals associated with user input.

22. The system of claim 1, wherein the one or more controllers configured to receive one or more signals of at least one of the one or more sensors and to transmit using at least one of the one or more transmitters one or more signals comprises:
one or more controllers configured to receive one or more signals associated with at least one of the one or more light sources.

23. The system of claim 1, wherein the one or more controllers configured to receive one or more signals of at least one of the one or more sensors and to transmit using at least one of the one or more transmitters one or more signals comprises:
one or more controllers configured to communicate using one or more optical signals, radio signals, wireless signals, hardwired signals, infrared signals, ultrasonic signals, and/or acoustic signals.

24. The system of claim 1, wherein the one or more controllers configured to receive one or more signals of at least one of the one or more sensors and to transmit using at least one of the one or more transmitters one or more signals comprises:
one or more controllers configured to transmit one or more signals for facilitating release of one or more quantities of nitric oxide.

25. The system of claim 1, wherein the one or more controllers configured to receive one or more signals of at least one of the one or more sensors and to transmit using at least one of the one or more transmitters one or more signals comprises:
one or more controllers configured to transmit one or more signals for facilitating one or more time schedules of nitric oxide release.

26. The system of claim 1, wherein the one or more controllers configured to receive one or more signals of at least one of the one or more sensors and to transmit using at least one of the one or more transmitters one or more signals comprises:
one or more controllers configured to transmit one or more signals for facilitating one or more specific durations of nitric oxide release.

27. The system of claim 1, wherein the one or more controllers configured to receive one or more signals of at least one of the one or more sensors and to transmit using at least one of the one or more transmitters one or more signals comprises:

one or more controllers configured to wirelessly receive one or more signals of at least one of the one or more sensors.

28. The system of claim 1, wherein the one or more controllers configured to receive one or more signals of at least one of the one or more sensors and to transmit using at least one of the one or more transmitters one or more signals comprises:

one or more controllers configured to control at least one of the one or more light sources based upon one or more signals of at least one of the one or more sensors.

29. The system of claim 1, wherein the one or more controllers configured to receive one or more signals of at least one of the one or more sensors and to transmit using at least one of the one or more transmitters one or more signals comprises:

one or more controllers configured to control at least one of the one or more light sources based upon one or more program instructions.

30. The system of claim 1, wherein the one or more light sources configured to facilitate release of nitric oxide from at least one of the one or more photolyzable nitric oxide donors in response to at least one of the one or more signals of the one or more controllers comprises:

one or more light sources configured to facilitate release of nitric oxide from at least one of the one or more photolyzable nitric oxide donors in response to one or more wireless signals.

31. The system of claim 1, wherein the one or more light sources configured to facilitate release of nitric oxide from at least one of the one or more photolyzable nitric oxide donors in response to at least one of the one or more signals of the one or more controllers comprises:

one or more light sources configured to maintain one or more concentrations of nitric oxide in response to at least one of the one or more signals of the one or more controllers.

32. The system of claim 1, wherein the one or more light sources configured to facilitate release of nitric oxide from at least one of the one or more photolyzable nitric oxide donors in response to at least one of the one or more signals of the one or more controllers comprises:

one or more light sources configured to decrease and/or discontinue release of nitric oxide from at least one of the one or more photolyzable nitric oxide donors in response to at least one of the one or more signals of the one or more controllers.

33. The system of claim 1, wherein the one or more light sources configured to facilitate release of nitric oxide from at least one of the one or more photolyzable nitric oxide donors in response to at least one of the one or more signals of the one or more controllers comprises:

one or more light sources configured to increase release of nitric oxide from at least one of the one or more photolyzable nitric oxide donors in response to at least one of the one or more signals of the one or more controllers.

34. The system of claim 1, wherein at least one of the one or more sensors; the one or more controllers; and the one or more light sources are arranged with one or more substrates.

35. The system of claim 1, wherein at least one of the one or more sensors; the one or more controllers; and the one or more light sources are arranged with one or more bandages and/or patches.

36. The system of claim 1, further comprising:
one or more additional transmitters and/or receivers.

37. The system of claim 1, further comprising:
one or more remote transmitters and/or receivers.

38. The system of claim 1, further comprising:
one or more user interfaces.

39. The system of claim 1, further comprising:
the one or more photolyzable nitric oxide donors.

40. The system of claim 1, wherein at least a portion of the system is configured for placement in vivo.

41. The system of claim 1, wherein at least a portion of the system is implantable.

42. The system of claim 1, wherein at least a portion of the system is configured for arrangement with penile tissue.

* * * * *

UNITED STATES PATENT AND TRADEMARK OFFICE
CERTIFICATE OF CORRECTION

PATENT NO. : 7,897,399 B2
APPLICATION NO. : 12/005132
DATED : March 1, 2011
INVENTOR(S) : Hyde et al.

It is certified that error appears in the above-identified patent and that said Letters Patent is hereby corrected as shown below:

Column 1, line 21 text currently reads as "naming Roderick A. Hyde as inventor" should be changed to --naming Roderick A. Hyde, Muriel Y. Ishikawa and Lowell L. Wood, Jr. as inventors--

Column 1, line 29 text currently reads as "naming Roderick A. Hyde as inventor" should be changed to --naming Roderick A. Hyde, Muriel Y. Ishikawa and Lowell L. Wood, Jr. as inventors--

Column 1, lines 37-38 text currently reads as "naming Roderick A. Hyde, Muriel Y. Ishikawa and Lowell L. Wood, Jr." should be changed to --naming Roderick A. Hyde, Muriel Y. Ishikawa, Leif T. Stordal and Lowell L. Wood, Jr.--

Column 1, lines 44-45 text currently reads as "naming Roderick A. Hyde, Muriel Y. Ishikawa and Lowell L. Wood, Jr." should be changed to --naming Roderick A. Hyde, Muriel Y. Ishikawa, Leif T. Stordal and Lowell L. Wood, Jr.--

Column 1, line 49 cancel the text beginning with "For purposes of the USPTO extra-statutory…" to and ending to Column 1, line 56 text "…to the benefit of the filing date."

Column 2, line 6 cancel text beginning with "For purposes of the USPTO extra-statutory…" to and ending to Column 2, line 38 text "…to the benefit of the filing date."

Signed and Sealed this
Thirty-first Day of May, 2011

David J. Kappos
*Director of the United States Patent and Trademark Office*